US009607041B2

(12) United States Patent
Himmelstein

(10) Patent No.: US 9,607,041 B2
(45) Date of Patent: Mar. 28, 2017

(54) SYSTEM AND METHOD FOR EFFICIENTLY ACCESSING INTERNET RESOURCES

(75) Inventor: Richard B. Himmelstein, Kure Beach, NC (US)

(73) Assignee: GULA CONSULTING LIMITED LIABILITY COMPANY, Dover, DE (US)

( * ) Notice: Subject to any disclaimer, the term of this patent is extended or adjusted under 35 U.S.C. 154(b) by 505 days.

(21) Appl. No.: 12/134,677

(22) Filed: Jun. 6, 2008

(65) Prior Publication Data

US 2009/0070434 A1 Mar. 12, 2009

Related U.S. Application Data

(60) Continuation-in-part of application No. 11/691,073, filed on Mar. 26, 2007, now Pat. No. 7,543,039, which is a division of application No. 09/585,151, filed on Jun. 1, 2000, now Pat. No. 7,272,637.

(60) Provisional application No. 60/942,318, filed on Jun. 6, 2007, provisional application No. 60/174,561, filed on Jan. 5, 2000, provisional application No. 60/143,982, filed on Jul. 15, 1999.

(51) Int. Cl.
| | |
|---|---|
| *G06F 15/16* | (2006.01) |
| *G06Q 30/00* | (2012.01) |
| *G06F 17/30* | (2006.01) |
| *H04L 12/58* | (2006.01) |
| *H04M 1/725* | (2006.01) |
| *H04W 40/24* | (2009.01) |

(52) U.S. Cl.
CPC ........ *G06F 17/30389* (2013.01); *G06F 17/30* (2013.01); *H04L 12/5895* (2013.01); *H04L 51/38* (2013.01); *H04M 1/72519* (2013.01); *H04W 40/246* (2013.01)

(58) Field of Classification Search
CPC ..... H04W 64/00; H04W 48/16; H04W 48/21; H04W 48/23; H04W 40/246; G06F 17/30; G06F 17/30389; H04M 1/72519; H04L 12/5895; H04L 51/38
USPC ................ 707/9; 709/217; 725/153; 368/10; 705/44; 340/539.13; 455/550.1, 89
See application file for complete search history.

(56) References Cited

U.S. PATENT DOCUMENTS

| | | | |
|---|---|---|---|
| 4,560,983 A | | 12/1985 | Williams |
| 4,706,121 A | * | 11/1987 | Young .................. G04G 15/006 340/4.37 |
| 4,890,315 A | * | 12/1989 | Bendixen .............. H04W 84/14 455/458 |

(Continued)

FOREIGN PATENT DOCUMENTS

WO    WO 9856159 A1    12/1998

OTHER PUBLICATIONS

The World Wide Web Consortium, "HTML 4.0 Specification," Apr. 24, 1998, 367 pages.

(Continued)

*Primary Examiner* — Viet Vu
*Assistant Examiner* — Michael A Chambers
(74) *Attorney, Agent, or Firm* — McAndrews, Held & Malloy, Ltd.

(57) ABSTRACT

A system, method and apparatus for efficiently accessing Internet resources are disclosed. The system, method and apparatus employ a portable device for receiving and transmitting information such as contact information, voting information and medical information, for example.

24 Claims, 15 Drawing Sheets

(56) References Cited

U.S. PATENT DOCUMENTS

| | | | |
|---|---|---|---|
| 5,202,828 A | 4/1993 | Vertelney et al. | |
| 5,259,017 A * | 11/1993 | Langmantel | H04W 84/16 |
| | | | 379/211.01 |
| 5,285,278 A * | 2/1994 | Holman | G06Q 20/3437 |
| | | | 348/465 |
| 5,293,645 A * | 3/1994 | Sood | G01S 5/021 |
| | | | 455/456.2 |
| 5,341,293 A | 8/1994 | Vertelney et al. | |
| 5,389,934 A * | 2/1995 | Kass | G01S 5/0009 |
| | | | 342/357.34 |
| 5,418,950 A | 5/1995 | Li et al. | |
| 5,451,839 A * | 9/1995 | Rappaport | H04B 17/20 |
| | | | 340/7.28 |
| 5,523,794 A * | 6/1996 | Mankovitz | G06K 17/0022 |
| | | | 348/478 |
| 5,572,726 A | 11/1996 | Hasuo | |
| 5,590,178 A * | 12/1996 | Murakami | H04L 12/58 |
| | | | 348/14.09 |
| 5,619,688 A | 4/1997 | Bosworth et al. | |
| 5,649,194 A | 7/1997 | Miller et al. | |
| 5,675,507 A | 10/1997 | Bobo, II | |
| 5,675,787 A | 10/1997 | Miller et al. | |
| 5,689,700 A | 11/1997 | Miller et al. | |
| 5,752,025 A | 5/1998 | Shakib et al. | |
| 5,752,253 A | 5/1998 | Geymond et al. | |
| 5,778,367 A * | 7/1998 | Wesinger, Jr. | G06F 17/3089 |
| 5,781,101 A * | 7/1998 | Stephen | G08B 25/016 |
| | | | 340/286.01 |
| 5,787,440 A | 7/1998 | Bakke et al. | |
| 5,793,966 A * | 8/1998 | Amstein | G06F 17/3089 |
| | | | 707/E17.116 |
| 5,802,518 A * | 9/1998 | Karaev | G06F 17/30448 |
| 5,805,581 A * | 9/1998 | Uchida | H04B 7/18532 |
| | | | 370/335 |
| 5,809,415 A | 9/1998 | Rossmann | |
| 5,812,776 A * | 9/1998 | Gifford | G06F 17/30887 |
| | | | 707/E17.115 |
| 5,826,034 A | 10/1998 | Albal | |
| 5,826,039 A * | 10/1998 | Jones | H04L 12/58 |
| | | | 707/999.006 |
| 5,832,386 A * | 11/1998 | Nojima | H04M 1/2745 |
| | | | 455/421 |
| 5,835,089 A | 11/1998 | Skarbo et al. | |
| 5,850,433 A * | 12/1998 | Rondeau | G06Q 30/02 |
| | | | 379/216.01 |
| 5,877,746 A | 3/1999 | Parks et al. | |
| 5,918,225 A | 6/1999 | White et al. | |
| 5,923,736 A | 7/1999 | Shachar | |
| 5,929,852 A * | 7/1999 | Fisher | G06F 9/52 |
| | | | 715/739 |
| 5,930,474 A | 7/1999 | Dunworth et al. | |
| 5,950,193 A | 9/1999 | Kulkarni | |
| 5,974,416 A * | 10/1999 | Anand | G06F 17/30569 |
| | | | 707/770 |
| 5,982,520 A * | 11/1999 | Weiser | G06F 1/1626 |
| | | | 398/107 |
| 5,987,440 A * | 11/1999 | O'Neil | G06Q 10/10 |
| | | | 705/39 |
| 6,016,488 A | 1/2000 | Bosworth et al. | |
| 6,041,325 A | 3/2000 | Shah et al. | |
| 6,073,138 A | 6/2000 | de l'Etraz et al. | |
| 6,085,084 A * | 7/2000 | Christmas | H04W 12/12 |
| | | | 455/411 |
| 6,085,242 A | 7/2000 | Chandra | |
| 6,091,957 A * | 7/2000 | Larkins | G01S 5/02 |
| | | | 455/456.2 |
| 6,094,649 A | 7/2000 | Bowen et al. | |
| 6,131,096 A | 10/2000 | Ng et al. | |
| 6,147,773 A | 11/2000 | Taylor et al. | |
| 6,151,386 A * | 11/2000 | Argade | H04M 1/6505 |
| | | | 379/70 |
| 6,161,134 A | 12/2000 | Wang et al. | |
| 6,194,992 B1 * | 2/2001 | Short | G06F 17/30899 |
| | | | 235/380 |
| 6,202,156 B1 * | 3/2001 | Kalajan | H04L 29/06 |
| | | | 709/225 |
| 6,208,659 B1 | 3/2001 | Govindarajan et al. | |
| 6,209,026 B1 * | 3/2001 | Ran | G06Q 10/047 |
| | | | 702/3 |
| 6,236,365 B1 * | 5/2001 | LeBlanc | G01C 21/206 |
| | | | 342/450 |
| 6,247,043 B1 * | 6/2001 | Bates | G06F 17/30699 |
| | | | 707/E17.059 |
| 6,259,449 B1 | 7/2001 | Saxena et al. | |
| 6,269,369 B1 | 7/2001 | Robertson | |
| 6,307,849 B1 * | 10/2001 | Tiedemann, Jr. | H04W 52/40 |
| | | | 370/332 |
| 6,336,121 B1 | 1/2002 | Lyson et al. | |
| 6,344,855 B1 * | 2/2002 | Fisher | G06F 9/52 |
| | | | 345/501 |
| 6,374,259 B1 | 4/2002 | Celik | |
| 6,393,421 B1 * | 5/2002 | Paglin | H04L 29/12009 |
| 6,457,066 B1 | 9/2002 | Mein et al. | |
| 6,463,417 B1 * | 10/2002 | Schoenberg | G06F 19/322 |
| | | | 705/2 |
| 6,526,399 B1 | 2/2003 | Coulson et al. | |
| 6,609,148 B1 * | 8/2003 | Salo | H04L 29/06 |
| | | | 707/999.01 |
| 6,665,687 B1 | 12/2003 | Burke | |
| 6,671,350 B1 * | 12/2003 | Oxley | H04M 3/42 |
| | | | 379/38 |
| 6,701,485 B1 | 3/2004 | Igra et al. | |
| 6,754,665 B1 | 6/2004 | Kawamoto et al. | |
| 6,873,610 B1 * | 3/2005 | Noever | H04L 29/06 |
| | | | 370/338 |
| 6,883,000 B1 | 4/2005 | Gropper | |
| 6,976,268 B2 * | 12/2005 | Courtney | H04N 21/4147 |
| | | | 348/E5.006 |
| 7,289,971 B1 * | 10/2007 | O'Neil | G06Q 10/10 |
| | | | 705/39 |
| 7,978,564 B2 * | 7/2011 | De La Huerga | A61M 5/14212 |
| | | | 221/15 |
| 8,005,952 B2 * | 8/2011 | Kammer | H04W 28/20 |
| | | | 342/387 |
| 8,271,660 B2 * | 9/2012 | Schulzrinne | H04L 29/08072 |
| | | | 370/261 |
| 2001/0028308 A1 * | 10/2001 | De La Huerga | A61M 5/14212 |
| | | | 340/573.1 |
| 2001/0054142 A1 * | 12/2001 | Van Blarkom | G06F 21/6254 |
| | | | 713/151 |
| 2002/0112250 A1 * | 8/2002 | Koplar | G06K 19/07703 |
| | | | 725/153 |
| 2005/0048961 A1 * | 3/2005 | Ribaudo | H04M 3/42348 |
| | | | 455/419 |
| 2006/0189359 A1 * | 8/2006 | Kammer | H04W 52/0229 |
| | | | 455/574 |
| 2008/0188261 A1 * | 8/2008 | Arnone | H04W 4/02 |
| | | | 455/550.1 |
| 2009/0161582 A1 * | 6/2009 | Kammer | H04W 28/20 |
| | | | 370/254 |
| 2009/0290695 A1 * | 11/2009 | Schulzrinne | H04L 29/06095 |
| | | | 379/93.02 |
| 2009/0294521 A1 * | 12/2009 | de la Huerga | A61J 1/035 |
| | | | 235/375 |
| 2009/0298514 A1 * | 12/2009 | Ullah | G01S 5/02 |
| | | | 455/456.5 |
| 2010/0097209 A1 * | 4/2010 | Wong | G01S 5/0284 |
| | | | 340/539.13 |

OTHER PUBLICATIONS

IBM Corporation, "HyperActions in a Markup Language," IBM Technical Disclosure Bulletin, vol. 30, Issue 1, Jan. 1, 1996, 1 page.

The Apache Software Foundation. "Module mod_log_common", publicly posted Oct. 28, 1996, <http://web.archive.org/web/19961028122916/www.apache.org/dosc/mod_log_common.html>.

(56) References Cited

OTHER PUBLICATIONS

Dar, Shaul et al. "DTL's DataSpot: Database Exploration Using Plain Language", Proceedings of the 24th VLDB Conference, New York, USA, 1998, pp. 645-648.
Howe, Denis, "Distributed Database", publicly posted Dec. 7, 1994, 1 page.
W3Schools.com. "SQL The Select Statement", retreived from <www.w3schools.com/sql/sq_select.asp>, 3 pages.
The home page for "Dogpile.com", captured Jan. 16, 1999, retrieved from <web.archive.org/web/19990116222229/http://www.dogpile.com/>.

* cited by examiner

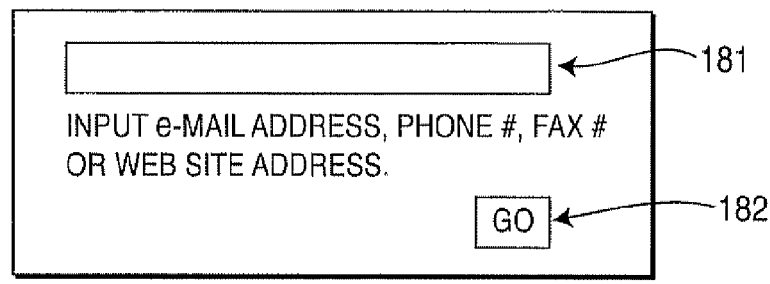
*FIG. 3A*
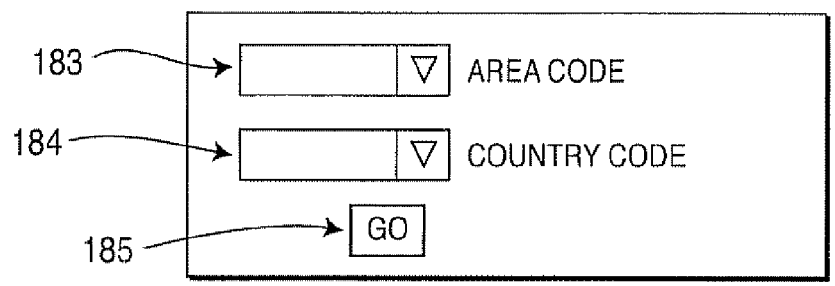
*FIG. 3B*
*FIG. 3C*

| | | |
|---|---|---|
| | • NAME | JOHN SMITH |
| 196 → | • e-MAIL ADDRESS | JSMITH@AOL.COM |
| 197 → | • MOBILE PHONE # | 888-242-2125 |
| | • PHONE # (HOME) | 601-212-1125 |
| 198 → | • PHONE # (WORK) | 601-433-7126 |
| 199 → | • FAX # | 601-717-1111 |
| | | 222 PARK AVE |
| | | GREENTOWN, NJ 07112 |

*FIG. 3D*

| XYZ COMPANY EMPLOYEE | | |
|---|---|---|
| NAME | HOME ADDRESS | e-MAIL |
| TOM ABBET | N/A | TABBET@XYZ.COM (CEO) |
| DEBBIE CASTER | N/A | DEBBIEC@AOL.COM (CUSTOMER SERVICE) |
| DAN TAYLOR | N/A | DTAYLOR@VERIZON.NET (MARKETING MANAGER) |

*FIG. 3E*

| | |
|---|---|
| BEST BUY | 121 MARKET ST. PHILADELPHIA |
| • PHONE # | |
| • FAX # | |
| BEST BUY | 247 CHESTNUT ST. PHILADELPHIA |
| • PHONE # | |
| • FAX # | |
| BEST BUY | 14 FONT ST. PHILADELPHIA |

*FIG. 3F*

LIST OF RETRIEVED DATA DISPLAYED IN SCREEN

SYSTEM AND METHOD FOR EFFICIENTLY ACCESSING INTERNET RESOURCES

CROSS-REFERENCE TO RELATED APPLICATION

The present application claims priority to U.S. provisional application Ser. No. 60/942,318, filed Jun. 6, 2008 entitled "SYSTEM AND METHOD FOR EFFICIENTLY ACCESSING INTERNET RESOURCES, and is continuation-in-part of U.S. non-provisional application Ser. No. 11/691,073, issued as U.S. Pat. No. 7,543,039, filed Mar. 26, 2007, and entitled "SYSTEM AND METHOD FOR A SOCIAL NETWORK," which is a divisional of U.S. non-provisional application Ser. No. 09/585,151, issued as U.S. Pat. No. 7,272,637, filed Jun. 1, 2000, and entitled "COMMUNICATION SYSTEM AND METHOD FOR EFFICIENTLY ACCESSING INTERNET RESOURCES," which claims priority to U.S. provisional application Ser. No. 60/143,982, filed Jul. 15, 1999 and to U.S. provisional application Ser. No. 60/174,561, filed Jan. 5, 2000. The entirety of the above-referenced applications are incorporated by reference herein for all purposes.

BACKGROUND

The disclosed systems and methods permit internet users to access network resources more efficiently. Particularly, the disclosed system uses unique individual identifiers, such as a phone number or facsimile number, as the primary search keyword to access internet resources and selectively access additional internet resources as desired by the individual. Using the system, an individual may also perform various functions such as placing a telephone call, or sending a fax or e-mail with a single selection (i.e., "one click"). This permits individuals to browse or otherwise "surf the net" faster.

The internet is a global computer network that connects all different types of operating systems and networks. It not only provides the physical backbone connections among networks, but also establishes the standard formats that enable different networks to communicate and share information. For example, the simple mail transfer protocol (SMTP) is the Internet e-mail standard that specifies the format of a messages so that a user on one computer network may successfully transfer mail to a user on another network. Without the SMTP, different networks which create their own e-mail message formats could only be understood if the e-mail receiver used the same type of network as the sender, or the receiving network had a plurality of different e-mail format converters to interpret different formats of incoming e-mail messages.

Each network e-mil application which uses the internet converts mail originating on the network from the format that the network uses into SMTP format before transmission over the internet, and each receiving e-mail application converts the SMTP formatted e-mail into its format. Therefore, instead of having many different types of e-mail message converters for each different e-mail format, different network e-mail applications can communicate using a single SMTP format converter. The same principle also be can applied to transferring data files among different networks.

Electronic mail is the most widely used application on the internet. Each receiver has to have an unique internet e-mail address for proper e-mail delivery. An internet user typically establishes an e-mail address by subscribing to an internet service from an internet service provider (ISP) who provides the host and gateway functions to the internet for the user. An ISP can be a university, a government entity, a private corporation or a commercial service provider. The provider will assign each user a unique e-mail address. No two users should have the same e-mail address unless they desire to be treated as a single entity by the internet.

The characteristics of e-mail address syntax and structure are well defined. An e-mail address consists of a unique combination of several terms. For example, when John Smith signs up with America Online® (AOL) as his internet service provider, John Smith will select a first portion of his e-mail address and will be assigned a second portion of his e-mail address. If John Smith's e-mail address is JSMITH@aol.com; "aol" is the abbreviation of America Online; "com" indicates that America Online is a commercial website; and JSMITH is the local part of the e-mail address E-mail that is sent to JSMITH@aol.com will first be forwarded to the host AOL domain, aol.com, and then AOL will further delivery the e-mail to the mailbox JSMITH. Although the domain part plus the local part of an e-mail address such as JSMITH@aol.com is a much easier format to memorize than the actual 32 bit internet mailbox address, (as dotted decimal notation 247.012.123.1 14), several difficulties still exist.

First, there is no consistent rule for naming a local part of a user's mailbox. In the AOL example, the local part is made of the first character of John's first name in combination with his last name, i.e., JSMITH. Once JSMITH is assigned to John on the aol.com domain, other John Smiths, a Joan Smith or a Joe Smith on the aol.com domain must choose a user name other than JSMITH to distinguish between themselves. Moreover, thousands of other ISPs use different ways to name their users' local part. It is almost impossible to guess the local part of a user even if his or her name is known. Non-alphanumeric characters, such as @, ˆ of % could be used in the e-mail address. Foreign ISPs and foreign e-mail addresses can also have non-English characters. Accordingly, it is difficult for an internet user to memorize a plurality of different e-mail addresses.

In contrast, due to their ubiquitous use and uniformity, phone numbers and facsimile numbers consist of a universally accepted digital number scheme which males the numbers easier to remember. Additionally, phone numbers and their owners are readily available through many information sources including phone books, phone number CDs or even internet sites that provide such information.

There are several prior art system which attempt to help an internet user access the address of other internet users more easily. For example, U.S. Pat. No. 5,826,039 to Jones discloses a universal networking directory service. A sender provides information regarding a particular receiver, such as the person's name, city and the state of residency, and the system retrieves the receiver's proper internet address. The sender can then use this address to contact the receiver.

U.S. Pat. No. 5,850,433 to Rondeau discloses an online electronic directory service. The service includes a dedicated server and a database similar to the paper yellow pages, which permit a user calling the database to be connected directly to the selected entity. A user can retrieve information from the database by entering different search parameters. Once the user reviews the results of the particular query and selects an entity, the server automatically places a telephone call to the select entity.

U.S. Pat. No. 5,778,367 to Wesinger, Jr., et al discloses a directory service which lets each individual user forward information to be electronically published. The information is automatically classified and then stored in a database. Other users might then search the database by specifying different parameters including name, title, phone number, facsimile number and e-mail address. The users fill in information regarding their fields of interest and the directory service returns entries having matching information for those fields.

U.S. Pat. No. 5,590,178 to Murakane discloses a service which links an e-mail system with a telephone system. The system retrieves all e-mail corresponding to a particular phone number to be automatically displayed when a telephone call to the particular phone number is placed or received.

U.S. Pat. No. 5,812,776 to Gifford discloses a method for a user to access web pages by either using a telephone number or descriptive term relating to the searching company or product. However, this system only retrieves the web page without further processing or analysis.

Although many of these prior art systems permit a user to access websites based upon selected information, these systems do not permit users to capture selected portions of those websites for further processing.

SUMMARY

One example method for providing access to information in a database comprises presenting a list of at least one user on a mobile device; receiving a selection of a target user from the list of at least one user; receiving a selection of information to be transmitted to the target user; receiving authorization to transmit the information; transmitting the information to the target user; and receiving verification of receipt by the target user. The list of at least one user may be constructed based on a location of each user in the list. The information may comprise, for example, medical information, contact information, a redeemable coupon, voting information or other information.

One example apparatus for providing access to information in a database comprises a processor, an input device, an output device, a receiver, a transmitter and a memory. The memory is operatively connected to the receiver, the input device, the output device, the receiver and the transmitter. The memory stores instructions operable with the processor to cause the processor to perform: presenting a list of at least one user on the output device; receiving from the input device a selection of a target user from the list of at least one user; receiving from the input device a selection of information to be transmitted to the target user; receiving from the input device authorization to transmit the information; transmitting from the transmitter the information to the target user; and receiving from the receiver verification of receipt by the target user.

Accordingly, it is an objective of the disclosed methods, systems and apparatuses are to use a provide users of mobile devices the ability to send/receive information to/from other users.

BRIEF DESCRIPTION OF THE DRAWINGS

FIGS. 3A-3F are diagrams illustrating internet database access through phone number or facsimile number search.

DETAILED DESCRIPTION OF THE PREFERRED EMBODIMENTS

Figure 1:
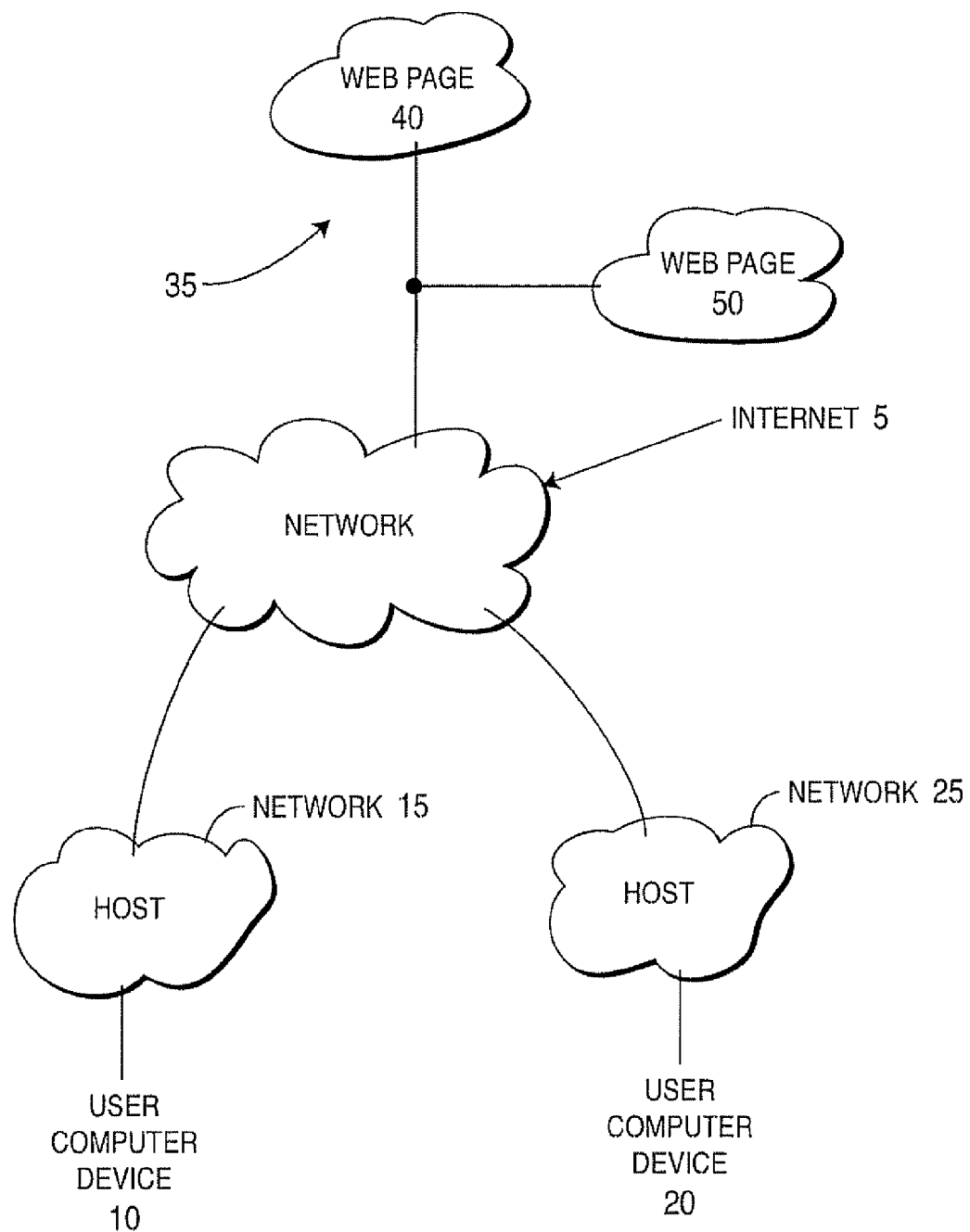
FIG. 1 is an overview of the internet.

Various examples of the disclosed systems and methods are described with reference to the drawing figures where like numerals represent like elements throughout.

Referring to FIG. 1, a plurality of networks 15, 25,35 and web pages 40 and 50 are shown connected to the internet 5. A first user 10 is a resident on a first network 15 and a second user 20 is a resident on a second network 25. Even if the two networks 15, 25 are different types of networks, (for example if network 15 is an Ethernet-based Novell network and network 25 is a token ring-based Microsoft Window NT network), utilizing the internet 5 the users 10, 20 may communicate via e-mail and perform file transfers. This is achieved by each network 15, 25, 35 converting outgoing data into a standard format such as SMTP, and converting incoming data from the standard format into the format for the particular network 15, 25, 35. By specifying a particular e-mail address or a designated web address, an internet user 10, 20 may compose and transmit an e-mail and the internet 5 will automatically route the e-mail to the particular user, or automatically route the desired content of the web page 40, 50 to the requesting user.

The disclosed system can run as a module or as part of an application utilized by an internet service provider (ISP), may interface with various kinds of software applications or may run as a "stand alone" package. It may be accessed using various interfacing devices such as a keyboard and mouse. For example, in one embodiment, selecting an icon displayed on a monitor screen activates the system.

Figure 2A:
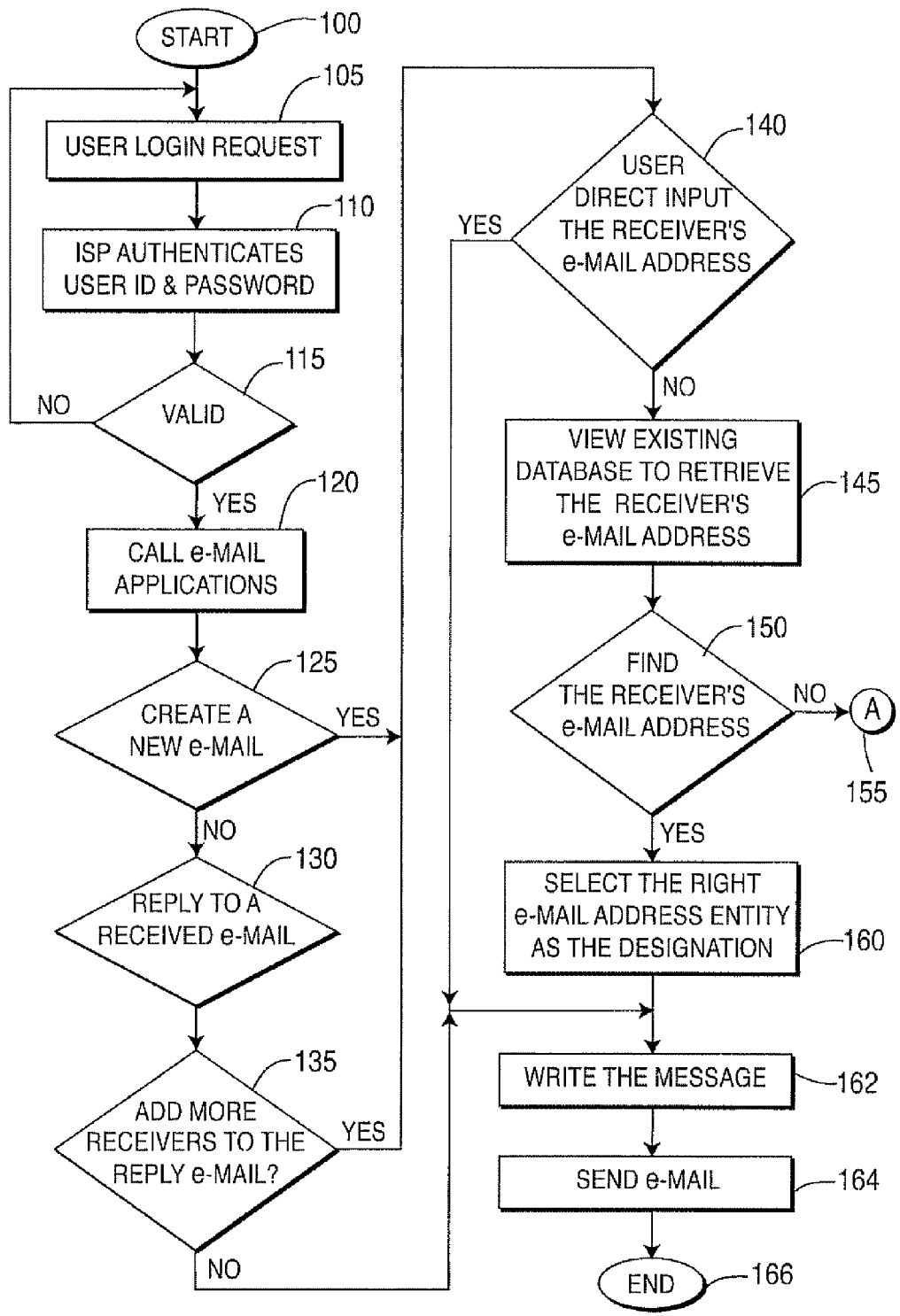
FIG. 2A is a flow diagram illustrating a regular e-mail sending procedure.

Referring to the flow diagram of FIG. 2A, utilizing a typical e-mail application, a sender logs onto the internet (step 105) by issuing an internet login request with his/her computer device to the ISP. The ISP verifies the validity of the user ID and password (step 110). If either the user ID or the password are incorrect (step 115), no access to the internet will be granted by the ISP. If the user ID and password are correct, the ISP connects the user to the internet 5. When the sender is ready to send an e-mail, the sender invokes the email application (step 120) and creates a new e-mail (step 125) or replies to a received email (step 130). The sender can directly enter the receiver's e-mail address if it is known (step 140). Otherwise, the sender can open and view an existing e-mail database (step 145), such as an address book, to determine if it contains the receiver's e-mail address. If the receiver's e-mail address is found (step 160), the sender writes the message (step 165) and sends the e-mail (step 170).

Figure 2B:
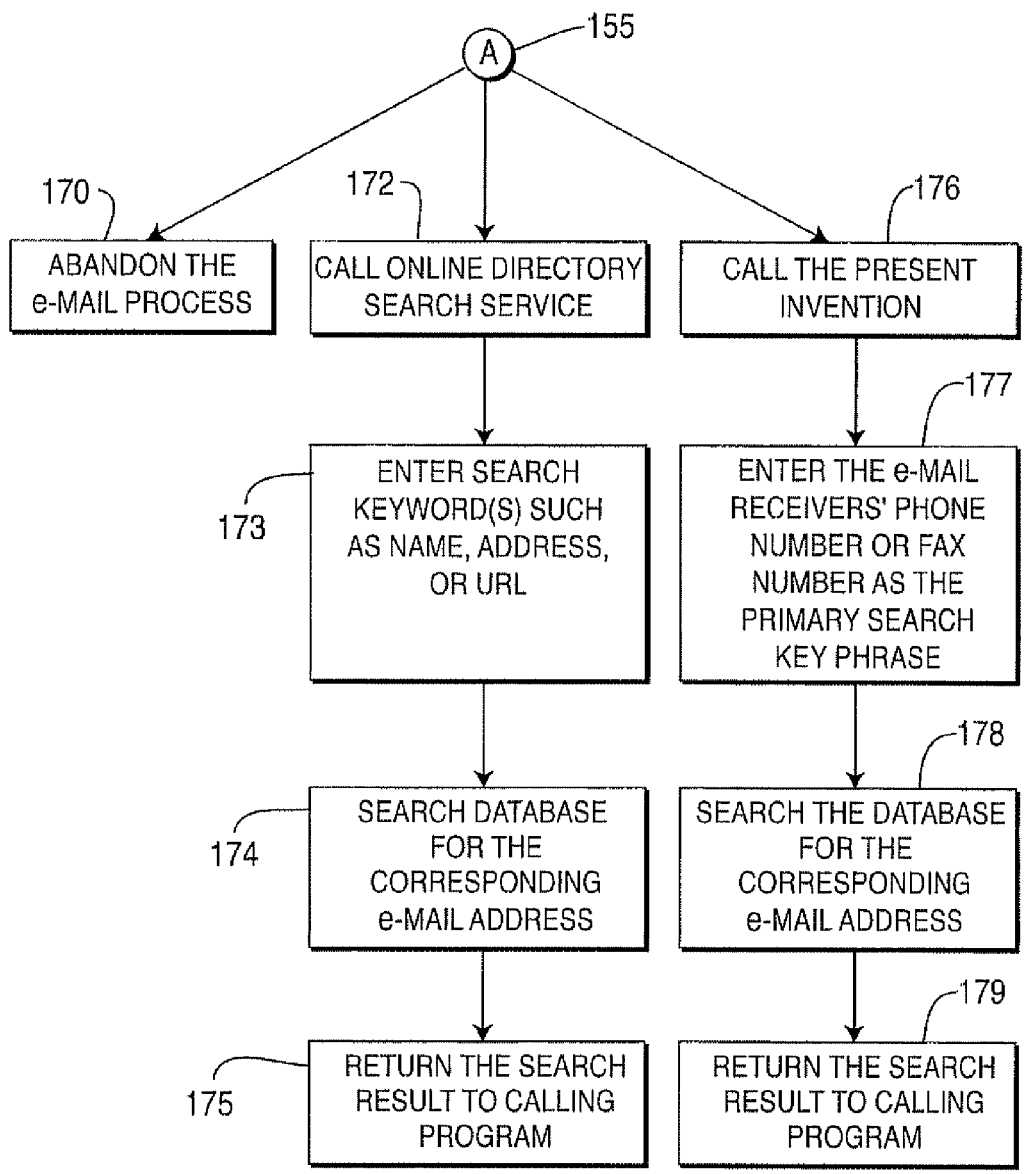
FIG. 2B is a diagram illustrating different ways to retrieve e-mail address by the prior art and the present invention.

If the sender does not know, and cannot find the receiver's e-mail address from the database of e-mail addresses, then the sender has three alternatives (step 155). As shown in FIG. 2B, in the first alternative the e-mail process is abandoned (step 160). In the second alternative the sender may access an online directory service (step 165) and retrieve the corresponding e-mail address by specifying various keywords (step 166) and searching a database (step 167). The keywords can be the receiver's name, address, URL or other unique identifying information. This alternative can be invoked from a calling program whereby the online directory service will return the proper e-mail address to the sender (step 168). The third alternative activates the system (step 170), whereby the user inputs the receiver's phone number or facsimile number as the keyphrase (step 171) to search the database for the receiver's e-mail address (step 172). The system then returns the search results to the user (step 173) to populate the data table. This procedure will be described in greater detail hereinafter.

Referring to FIG. 3A, the system has "intelligent" features which makes the search for an e-mail address or other unique individual identifiers transparent to the user. For example, instead of using separate input fields for e-mail addresses, phone numbers, facsimile numbers or website addresses, the screen display has only a single input field 181. A user can type in an e-mail address, website address, phone number or facsimile number into the input field, then select the GO 182 button in FIG. 3A. If the search results in more than one match based on more than one unique keyword selected, the system may prompt the user to narrow down on select one of the matches. For example, if the user selects a keyword such as 1-800-CALL-NOW, the system may return with two different results: 1) a phone number; and 2) a website. The user is prompted to choose whether the key phrase is a website or a phone number. The system could then do a search based on the additional information and search again. Alternatively, the system may display all selections for the user to choose.

Referring to FIG. 3B, the user can further input area code 183 or country code 184 for this particular phone or facsimile number as an option and select the CO button 185 to invoke the application.

The system will search all relevant databases and retrieve relevant information that matches the specified key phrase. For example, a user inputs John Smith's phone number, 601-212-1125 (the dashes "-" can be created automatically by the system), in the input field 181 then selects the GO button 182 and the system searches for the phone number.

Referring to FIG. 3C, the system retrieves relevant information from one or multiple databases and displays all information that exists for the individual in the customized table including John's name, John Smith's e-mail address, phone number and facsimile number 188-195, The system retrieves this information based on the headings of the retrieve and display table. Because John Smith doesn't have a website address, the table indicates that the website not available 195. In one embodiment, a user can create different display tables or modify existing ones. Alternatively, the system may display the information without a table.

A simplified retrieve and display table 300 is shown in Table 1. This retrieve and display table includes fields such as name, e-mail address, mobile phone number, home phone number, work phone number, facsimile number and home address

TABLE 1

Name
E-Mail
Mobile Phone Number
Phone Number (Home)
Phone Number (Work)
Fax Number
Home Address If a user selected Table 1 as the retrieve and display table and inputs John's phone number or facsimile number as the search keyword, the system searches through relevant databases and retrieves John's name, e-mail address, mobile phone number, home phone number, work phone number, facsimile number and home address and displays them as shown in FIG. 3D. If a displayed item can lead to further action, the system indicates such. One manner is having a circular area displayed in front of the item which a user can select to invoke the further action. For example, referring back to FIG. 3D, John's e-mail address, mobile phone number, home phone number, work phone number and facsimile number all have the circular area 196, 197, 198 and 199 which precedes each item. A user can decide whether he wants to send John an e-mail, call John at his home, work or mobile phone or send a facsimile (by downloading the file to be faxed), by selecting the corresponding circular area. Alternatively, red or blue contrasting lettering may be used to indicate further action is available by clicking on the same.

The system interfaces with software modules that do the activity such as e-mail, call by phone or send a facsimile, or may incorporate its own module to do such. If a user and an individual being called both have equipment that permits video web phone applications, the system may automatically invoke the application in such a manner. The system permits an individual to use their e-mail address as their phone number or fax number, thereby permitting individuals to call or fax other individuals over the internet. The system can use an e-mail address as the keyword to then allow someone to chose options such as "phone", "facsimile" etc. The system can also use an individual's e-mail address to provide their corresponding physical address, such as their home address. The disclosed system retrieves information from relevant databases, either from the internet or a local computer, and displays results according to the retrieve and display table. The system can be expanded to include other unique identifiers such as pager numbers, cell phone numbers, vacation home phone numbers. If an item includes mole than one selection, for example if there are multiple vacation phone numbers for the particular user, the system can list all possible selections and provide a pull down menu for further selections.

The system is flexible in permitting a user to invoke the system even if the user is using an application, for example, a user is in the middle of composing an e-mail. The same user can invoke the system to make a phone call or send a facsimile to the same or other designations.

Referring back to FIG. 3C, another embodiment of the system, will invoke other applications either to direct dial the selected phone number for the user, dial and send a facsimile to the selected facsimile number, access the website or invoke an e-mail application. In the case where dialing a phone number or facsimile number is selected, if the phone number or facsimile number is shared by one organization, the organization directory can be further retrieved if the user has permission to access. This will be explained in greater detail below.

Referring to FIG. 3E, for example, a user inputs company XYZ's main phone number or facsimile number as the search keyword (i.e., unique individual identifier), the system displays a retrieved list of individuals at the organization with their individual e-mail addresses, and their title or specific information. Each name or department may be listed and followed by a field that provides basic information such as one's title, location, department etc. This information field may be maintained and size altered to accommodate a person's or company's needs. For example, one person's title may be "customer service". The user can select the desired method of contact such as selecting an e-mail address from the member list of the organization Of course, the retrieved and displayed information is based on the user requested and the restriction a data base owner/company puts on its database. If an individual or organization desires to be "unpublished" system can allow such.

For example, a user searches the main phone number of XYZ company inquiring a home address and e-mail address. Even though XYZ company has all of its employees' home addresses, XYZ company only allows certain designated employees' names and their e-mail addresses to be accessed, not their home address unless a person requesting the information has "priority access". Therefore, the user can see the display of employee names and e-mail addresses, while employees' home addresses are not available as shown in FIG. 3E. Individuals or companies setting up their database may determine different priority access levels for family, friends or employees. The system allows this to be set tip on an individual basis, family basis or employee basis and can require for security reasons that a user accessing the database information to submit his e-mail address or password for access. If XYZ is a franchise or chain store, the retrieved information can include information about other local, regional or national stores, such as location, phone numbers or website address, as shown in FIG. 3F. For example, if the user inputs one of the phone numbers of BEST BUY electronic stores in the Philadelphia area, the system will retrieve the address, phone number, and facsimile number of the particular BEST BUY store and display them. The system will phrase the user's input to decide whether the input is an e-mail, phone number, facsimile number or website address. If the user only entered a seven digit number, phone number or facsimile number then selected the phone or facsimile buttons, the system automatically prompts for the area code. A user can use the area code or country code option to specify the area where the search shall cover. The system my allow all area codes to be selected by input wildcard "*" in the area code field.

In an alternative embodiment, cell phones, home phones, vacation phones, separate work phones for husbands and wives, pagers and all e-mail addresses (i.e., work or home) may all be included in the table as well Any of these items, or future "communication" devices, could be sorted under one of five or more designated headings as follows: 1) name; 2) e-mail address; 3) website address; 4) phone number; and 5) facsimile number. For example, if government, medical or banking institutions chose to use an individuals' social security number as the major search key phrase, the system would interface with their database and, using the search key phrase, retrieve the requested information. For example, banks have various financial information sorted by credit cards, mortgages, bank accounts etc. Medical information can sort by entire medical history by doctor, or types of injuries or diseases/sicknesses from existing internet database organized with other key phrases.

The system permits a user to "surf the net" faster by providing an improved way of accessing the internet for general uses. If a user knows one particular information about a company, they can retrieve the company's phone number, facsimile number, e-mail number and website address, upon entering the particular information or description (i.e., unique individual identifier). If any information is not available for access or does not exist there, the system responds with either information is unavailable message or information may not exist message to the user.

If multiple "main" phone numbers, facsimile numbers, e-mail addresses or web addresses are retrieved, the system will first display phone number, then facsimile number, e-mil address and website address sorted in alphabetical order, but will first display 800 numbers and ".com" website addresses if they exist, and advise a user to select an option (down arrow) for more. If a user selects to send e-mail, a pull down menu can provide the user with an alphabetical sort of all individuals names with their home or work e-mail addresses along with a brief description such as name, title and location (if there are multiple business locations).

Figure 4A:
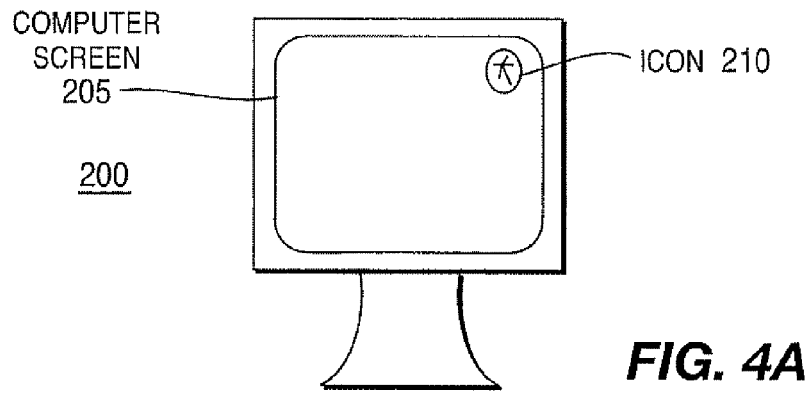
FIGS. 4A-4G aye detailed screen displays of a user interface employed by the example systems.
Figure 4B:
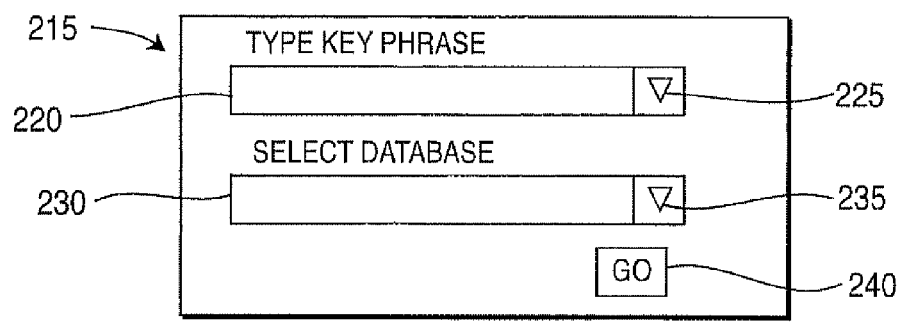
Figure 4C:
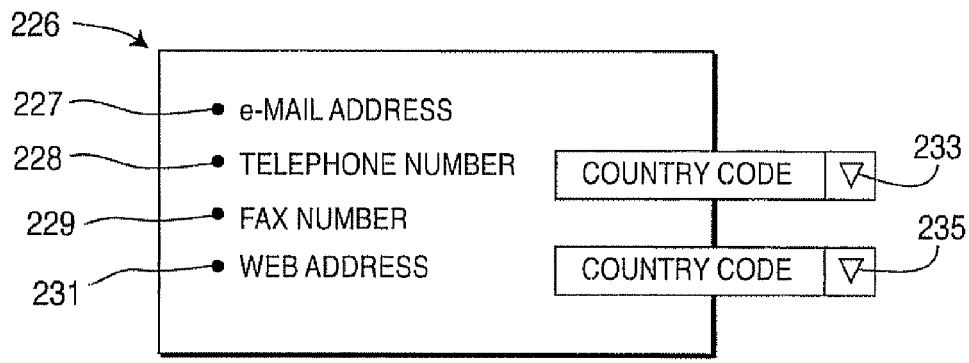
Figure 4D:
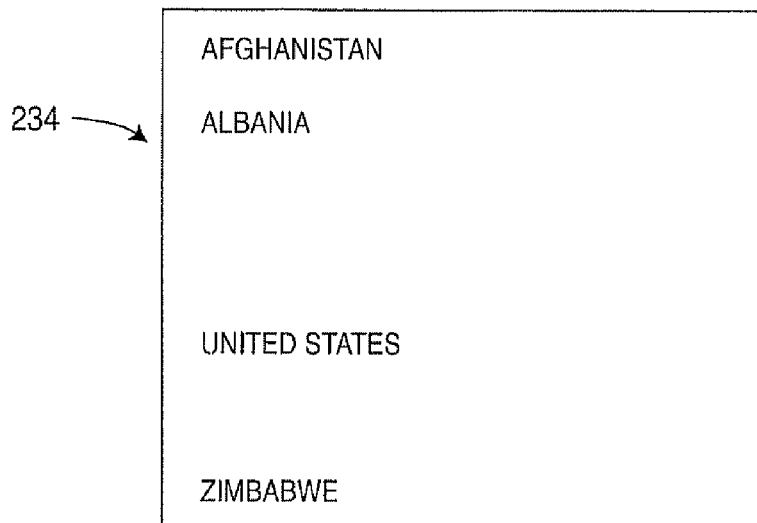
Figure 4E:
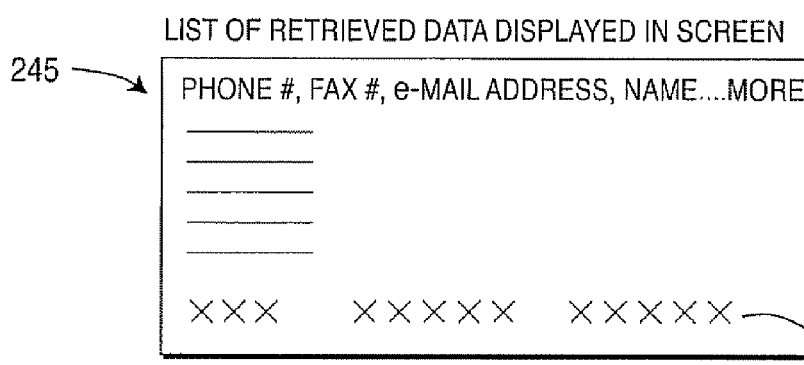

An alternative embodiment of the system having a graphical user interface (GUI) is shown in FIG. 4A. An icon 210 displayed on a monitor screen 205 represents the software application and is used to invoke the system. Assuming that the database of the system and/or the local database have been established, by directing a pointer to the icon 210 and selecting the icon, the system is invoked. A first example embodiment of the system using the GUI is shown in FIG. 4B. Referring back to FIG. 4B, the database can be selected by directly entering the name of the database, or selecting from an ISP database or a local database. By pointing and clicking on the option pull down menu area 235, the list of databases 235 will be displayed as shown in FIG. 4G. The user can select the database from which he or she will retrieve information. Once the user completes the selection of both the key phrase and the database, the user can select the GO icon 240. The results of the search based on the specified web address, e-mail address, phone number or facsimile number will be displayed 245 as shown in FIG. 4E. The user can view the display and select the correct entity. Alternatively, the system may, transparent to the user, merge all databases into one so that the user does not have to choose a particular database.

For example, if one database is created for a geographical area such as Philadelphia or New York, the system may merge the data and store in a single database that is searchable and retrievable. Optionally, the system may search all databases without being required to copy or reclass the information. Other valuable classifications may also be made, (such as a database for attorneys, a database for accountants, a database for retail companies, a database for technical companies and all other types of industries).

The system may provide the first level of information from its own database or subdatabase, a local database and, if additional information is requested, link to a company's database at the second level. The system may obtain the first level of information by using web-traversing program called robots or spiders which follow link after link within webpages across the internet. The web-traversing programs catalog documents and store information for transmission to a parent database, where the information is sifted, categorized and stored. After a web-traversing program has run, the database compiled through the efforts of the robots and spiders is searched using a database management system. Using keywords or search terms provided by a user, our system's database locates matches.

Referring back to FIG. 4B, the screen displayed 215 requires two inputs from the user: the key phrase 220 and the database to be searched 230. The key phrase 220 can be a phone number, a facsimile number, an e-mail address or a web address. By pointing and clicking on the pull down menu option area 225, the screen display 226 as shown in FIG. 4C is shown. The screen includes four key phrase types; 1) e-mail address 227; 2) telephone number 228; 3) facsimile number 229; and 4) web address 230. Additional key phrase "types" may be defined by the user. For example, "name" may be used as a fifth key phrase. The phone number and facsimile number may be combined for search purposes.

In the case where a phone number or a facsimile number is entered, the default designated county and area code for the phone number or the facsimile number is the same country and area code as the individual's ISP unless the user enters the area code and/or country code. The user may alternatively specify other country and area codes by pointing and clicking on the pull down menu option areas 232, 233. As shown in FIG. 4D, a list of countries 234 will be displayed. The user can select the designated country from the list 234 by clicking on same, and the corresponding country code will be incorporated into the phone number or the facsimile number. The user can select a designated area code in the same manner from the list 234 by clicking on same, and the corresponding area code will be incorporated into the phone number and facsimile number.

Figure 4F:
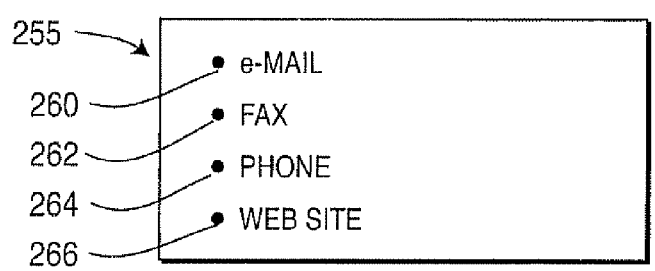
Figure 4G:
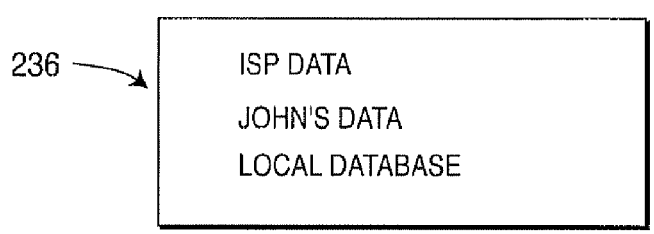

In another embodiment of this system, as shown in FIG. 4F, the screen display 255 further provides the user the option to select from sending e-mail 260, sending a facsimile 262, connecting a phone call 264 or accessing a website 266. This information can be continually displayed as the user is surfing the internet the information automatically changes in the table as the user retrieves new webpages. Optionally, once the relating information has been retrieved from the database and displayed on the screen, the user can select the desired one, then another display menu will pop up. Of course, a user can search and retrieve relevant information based on the content of the customized retrieve and display table. Nevertheless, in this example, only e-mail, facsimile numbers, phone numbers and website addresses are requested and displayed. The pop up menu offers four different selections in this example. A user can either send an e-mail by selecting the e-mail option, or sending a facsimile by selecting the facsimile selection, by connecting the phone call to the receiver, or, at last, connecting to the worldwide website by pointing and clicking the corresponding menu selections. If the retrieve and display is customized to display local telephone numbers, fax numbers, e-mail numbers, etc., the system in conjunction with the ISP and website can do such.

Figure 5A:
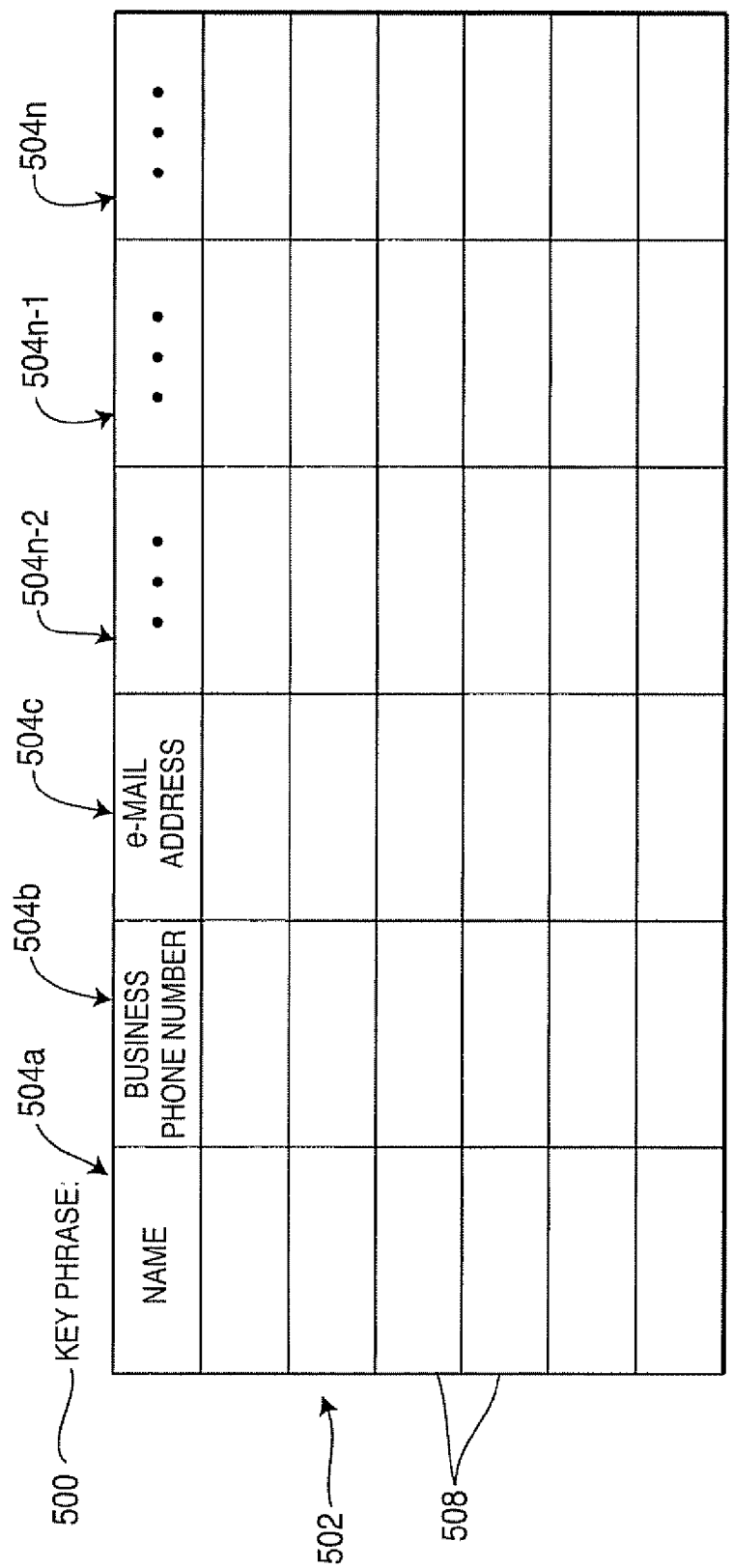
FIGS. 5A-5F are detailed screen displays of the system including a data table for selectively retrieving and displaying data in accordance with the disclosed systems.

Referring to FIG. 5A, the system utilizes key phrases 500 and a retrieve and display table 502 in order to improve the manner in which a user accesses the internet. The criteria for the search and the format of the information resulting therefrom can be entirely user-defined. The search criteria are based upon the key phrase 500. The results of the search populate the retrieve and display table 502 comprising columns 504 and rows 502. The columns $504_{a-n}$ may be defined by the user as shown in FIG. 5B.

Figure 5B:
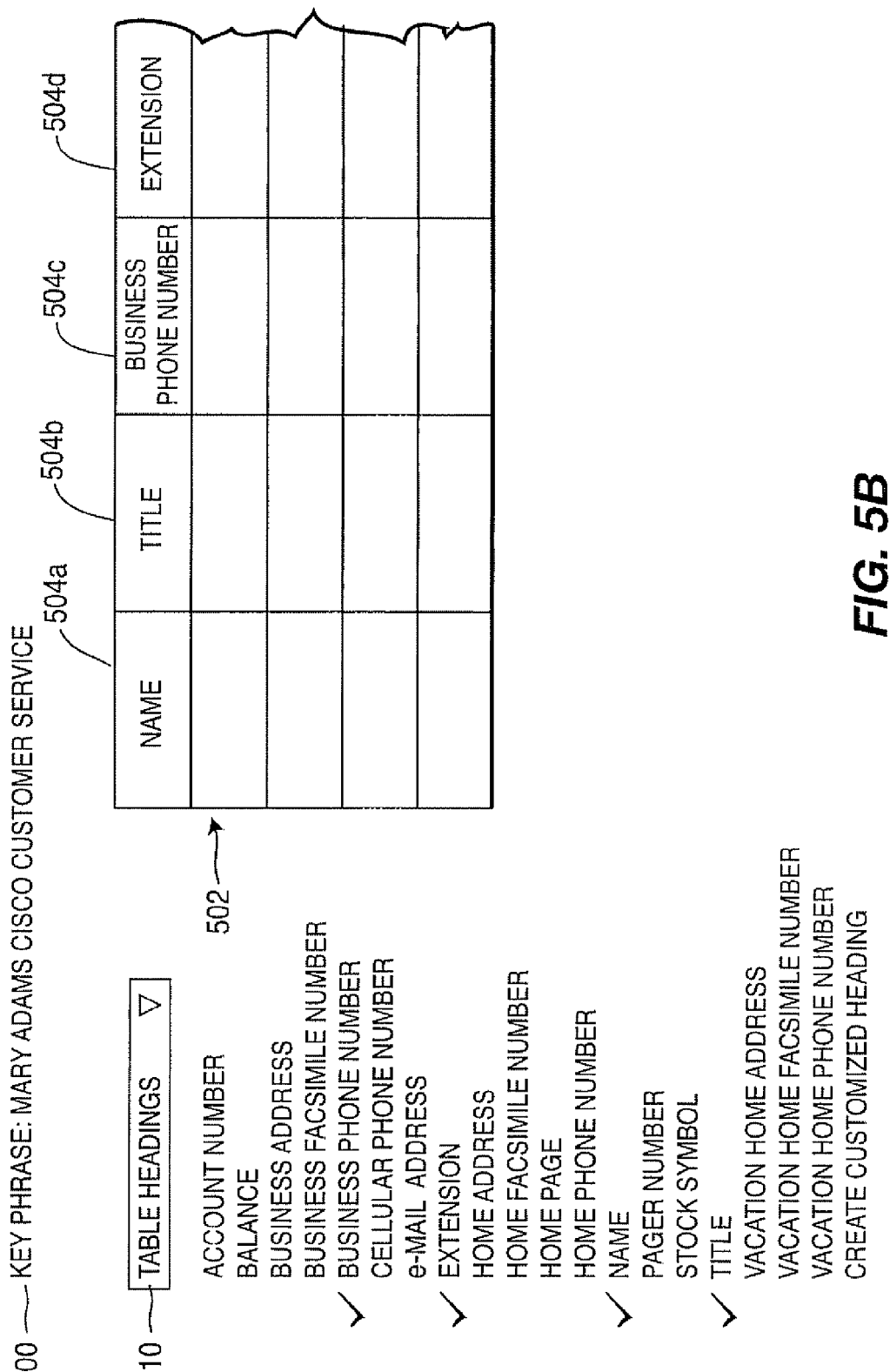

Referring to FIG. 5B, the user accesses a screen which lists both the key phrase 500 and table headings 510. As the user selects the different table headings 510, (for example, business phone number) extension, name and title), the corresponding columns $504_{a-d}$ appear in the table 502. The user can select from the plurality of predefined table headings 510, or may create their own headings and customize the table 502 according to their needs. In this manner, the system permits users to use one or more key phrases to obtain results in a systematic and organized fashion according to their needs. This is significantly different than present search engines which provide results in descending order of matching with the key words. The system will be explained in greater detail with reference to the following example.

Figure 5C:
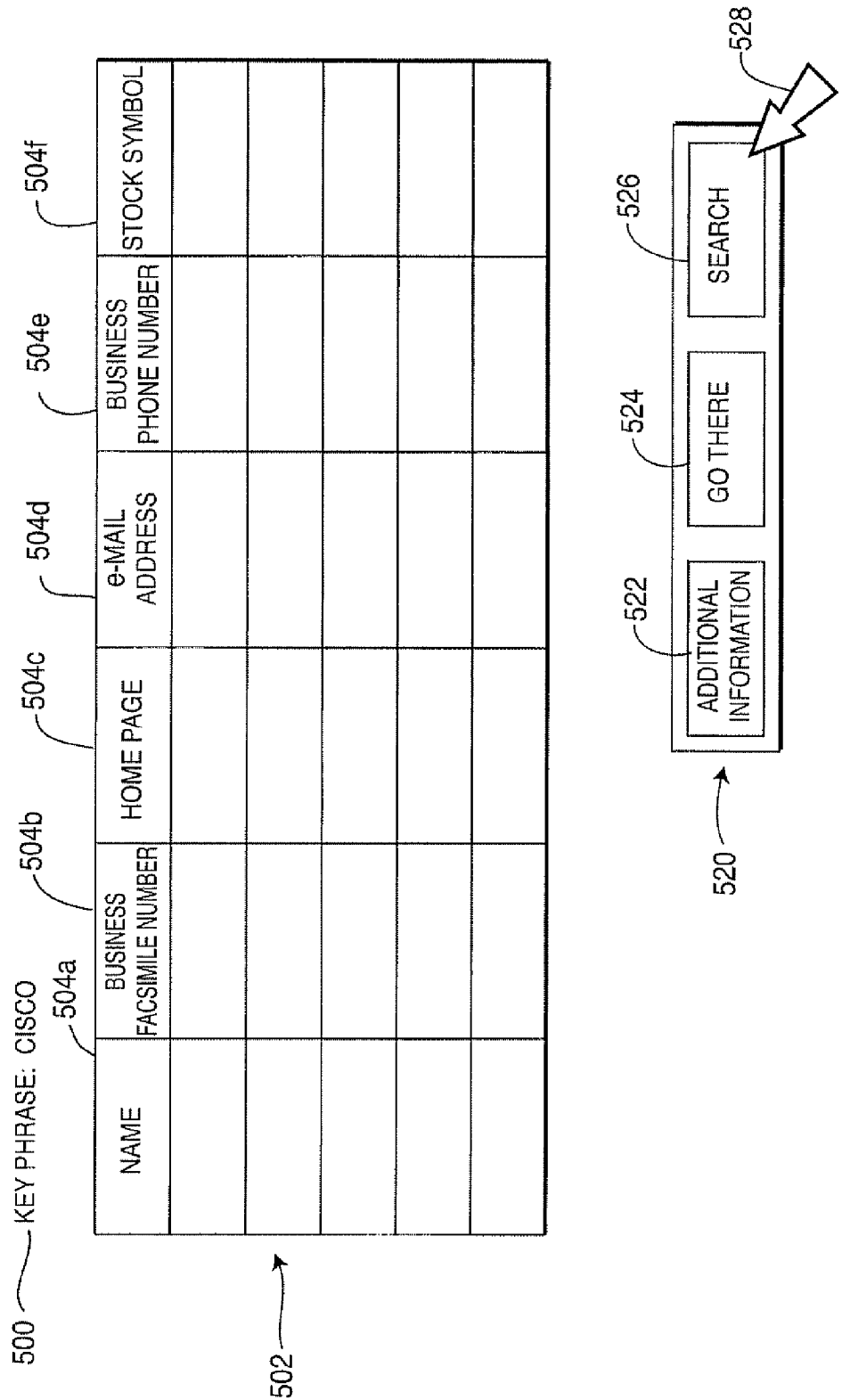
Figure 5D:
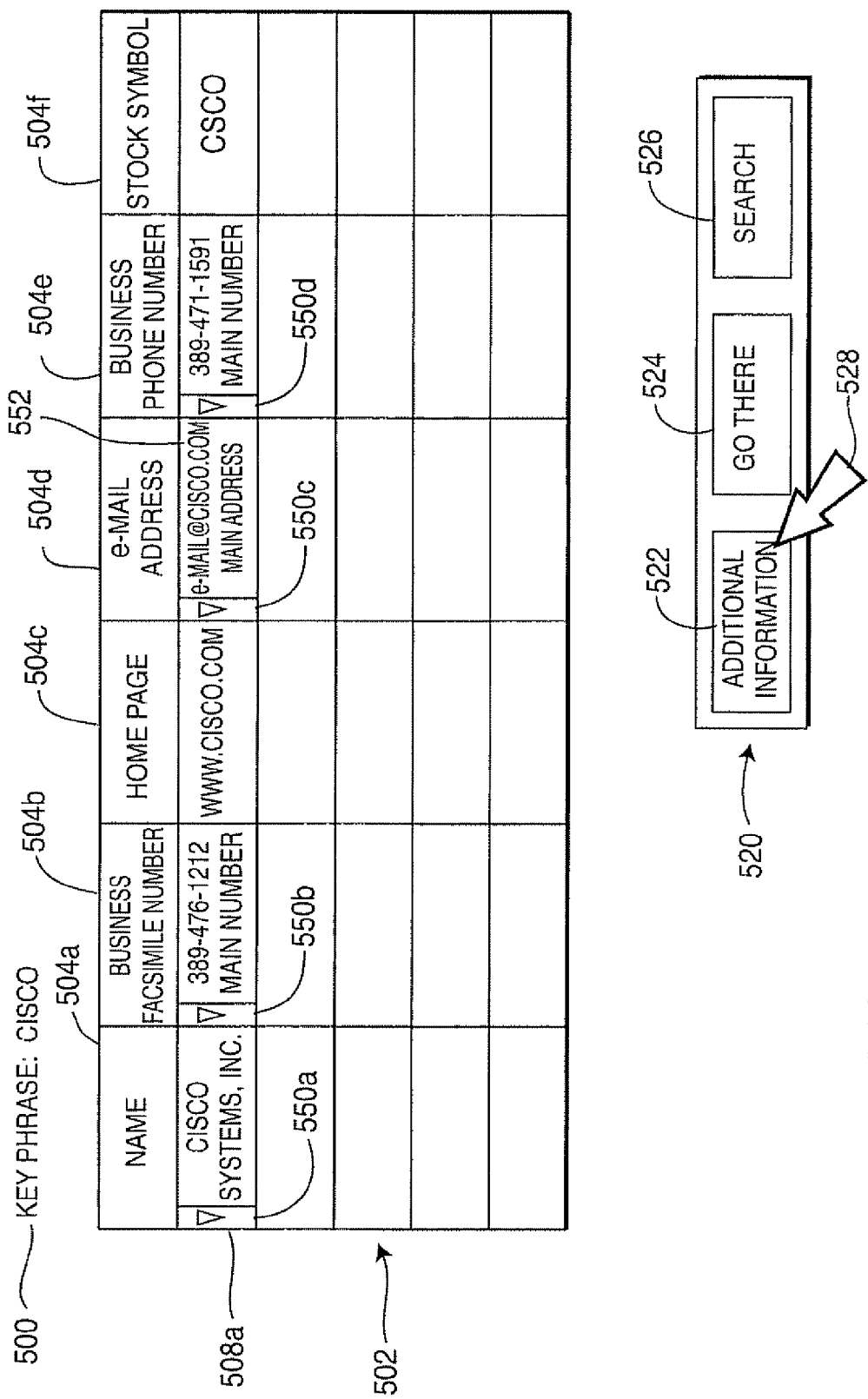
Figure 5E:
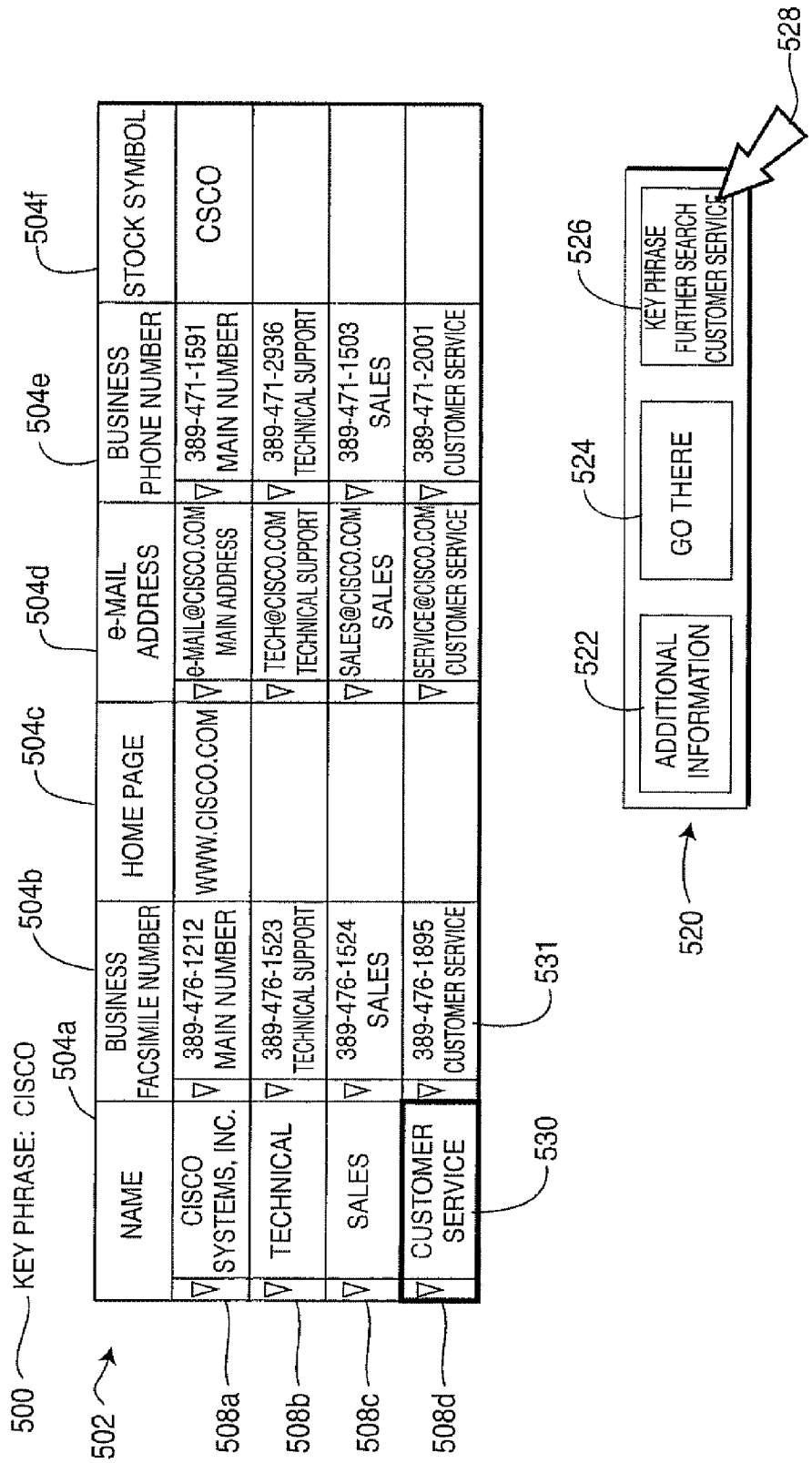

Referring to FIG. 5C, the key phrase 500 that has been selected is Cisco. The table 502 includes the table headings 510, (shown in FIG. 5B), name, business facsimile number, homepage, e-mail address, business phone number and stock symbol which provide the headings for the six columns $504_{a-f}$. After the user has input Cisco for the key phrase 500 and has created the table 502, they can select among three options within the activity menu 520. As will be explained in further detail, the three options are ADDITIONAL INFORMATION 522, GO THERE (i.e., perform function) 524, and SEARCH 526. In order to initiate the search, the Cursor 528 is moved to the SEARCH button 526 and selected. The search could also be automatic upon highlighting a specific cell and depressing the "return" button on the keyboard or double-clicking the mouse on the specific cell. Referring to FIG. 5D, the search results populate the cells in the first row $508_a$. As shown, a search is performed for the information that most closely matches the key phrase and also the particular columns $504_{a-f}$. In the embodiment that is shown, the system returns only the most relevant search results and places them in the cells in a single row $508_a$. Optionally, if additional information is available, such as multiple responses to the particular query, the ADDITIONAL INFORMATION button 522 is highlighted. If the user desires additional information regarding all columns $504_{a-f}$, the cursor 528 is moved to the ADDITIONAL INFORMATION button 522 and selected. This results in the table 502 shown in FIG. 5E. In this table 502, the cells in additional rows $508_{b-d}$ are populated if additional information for the particular column $504_{a-f}$ is available. As shown in FIG. 5E, additional information was available for this business facsimile number, e-mail address and business phone number column $504_b$, $504_d$, $504_e$. In this manner, a user can more easily get specific information regarding the departments or personnel that they wish to contact.

Referring back to FIG. 5D, the system indicates that additional information is available for selected fields by providing "down arrow" selection buttons $550_{a-d}$. In this manner, if a user wants additional information only regarding a specific column, the user selects the down arrow $550_{a-d}$ associated with that column. For example, if the user wants more information regarding the e-mail addresses $504_d$, they select the down arrow $550_c$. Only the additional information associated with that column $504_d$ will be presented. However, if the user selected down arrow $550_a$ for more information regarding Cisco Systems, this also results in the table 502 shown in FIG. 5E. Optionally, the user can select a particular cell, such as cell 552, and double-click on it to perform the particular function, which in this case is sending an e-mail.

Figure 5F:
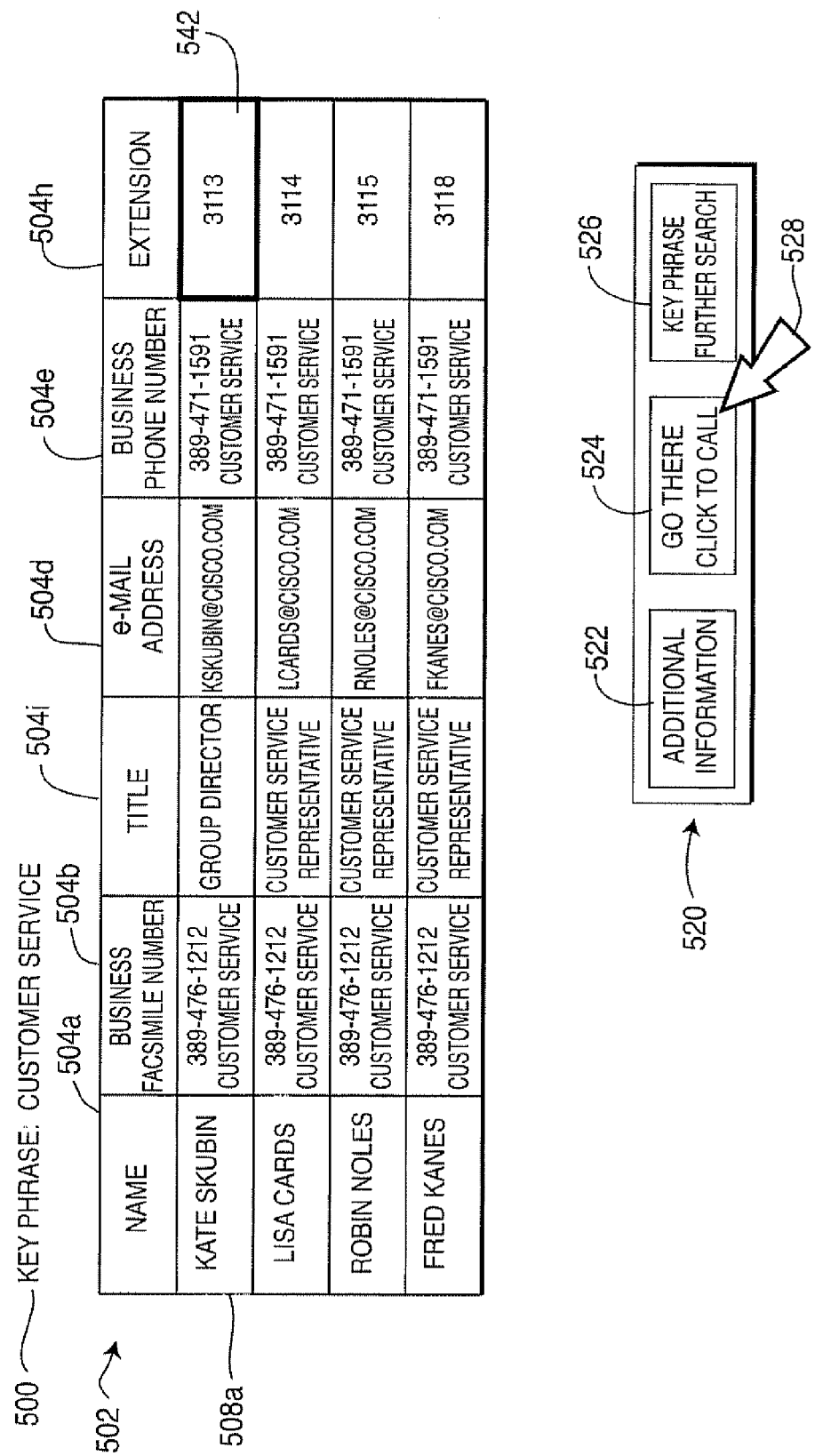

The user may also perform a subsearch, which uses the results of the earlier searches to further refine the search. For example, referring again to FIG. 5E, once all of the information for a particular key phrase has been obtained, the user may wish to further refine the results of their search. If the user desires to get more information regarding the customer service department's facsimile number, they move the cursor to the customer service cell 531 in column $504_b$ in row $508_d$. If the user desires more information regarding the customer service department, they can select cell 530 which becomes highlighted as shown, the cursor 528 is moved to the SEARCH button 526. As shown, the SEARCH button 526 has changed to indicate that the system is undertaking a further search using a new selected key phrase. The KEY PHRASE FURTHER SEARCH button 526 now includes the further key phrase "customer service". Accordingly, the KEY PHRASE FURTHER SEARCH button 526 is selected which results in the table shown in FIG. 5F. Since the key phrase is now customer service, the system populates the table 502 with the results of that key word search. As shown in FIG. 5F, the user can also modify the table 502 before or after they depress the KEY PHRASE FURTHER SEARCH button 526. In the example shown in FIGS. 5E and 5F, the user deleted column $504_h$ including stock symbol and added the column $504_f$ including the extension number, and deleted column $504_c$ for the homepage and added column $504_i$ with the title of the person. Accordingly, a table shown in FIG. 5F shows all of the information that user believes is relevant for their search on the personnel within the customer service department of Cisco.

As understood by those of skill in the art, the system may display a single row 508 at a time, (for example, row $508_a$ shown in FIG. 5E), and provide up and down arrows to scroll through all of the choices. Alternatively, only the cells that are populated are returned to the user. If the user would like to select a particular person to speak to, such as Kate Skubin, the group) director of customer service, the user can move the cursor 528 to column $504_h$ which lists the extension numbers for all of the employees. The user can then select the cell in first row $502_a$ of that column which lists the extension number for Ms. Skubin. Once this cell 542 has been highlighted, the cursor is then moved down to the GO THERE button 524. The GO THERE button 524 will change as shown in FIG. 5F to include the words "click to call". It should be noted that the selection of a particular cell for an extension will dial that extension if the user is on the same company phone system. Otherwise, the user would select a column heading such as direct inward dial (DID) number. This permits customers and other people "outside" the company's phone system to contact the personnel directly. It should be noted that the GO THERE button 524 will change depending on the action to be taken. For example, when the GO THERE button 524 is selected, the system places a call directly with Ms. Skubin. In the same manner, Ms. Skubin may be e-mailed or taxed depending upon the cell which is selected.

Although the disclosed system may search and retrieve information over the internet, one embodiment of the system builds a local database for search and retrieval using the standard selection heading shown in FIG. 5B. As explained earlier, web crawlers, robots or spiders are used to populate the main level of the database. The main level will be referred to hereinafter as "level 1". This can be graphically represented by $508_a$ in FIG. 5D. For example, a webcrawler searching the web and accessing webpages may be able to find a company's name, e-mail address, home page and phone number. The system may access other unrelated databases, such as an on-line financial database, to ascertain other information regarding the company, such as the company's stock symbol.

Alternatively, the data may be selectively input by companies that wish to participate and utilize the database services. For example, the data may be input manually by a company's employee, subcontractors and agents, and forwarded enmasse to a central website maintained for the purposes of creating a master database. The information in the database can then be available to all users to download to their local database. If a company participates in this manner, it may select from among the table headings in FIG. 5B and can create new headings. If standard table headings such as shown in FIG. 5B are not used, the headings created by a particular company must be correlated with the standard headings or new standard headings created to accommodate the entries by that company. Accordingly, the system provides the option of providing users with blank tables and selecting from among standardized headings, or permitting users to create their own headings.

For example, if a company wanted to have "president's office" on the first level with a phone number, fax number and e-mail address, they can customize the table headings prior to entering the information. The user can select "create customized heading" as shown in the table headings 510 of FIG. 5B. Alternatively, when a user is searching the information from a particular company, the table headings may note which field, if any, were created by the actual company. Further, when searching, a user can query the system to provide all applicable table headings available for a particular keyword (i.e., person or company).

When the system provides a "blank table" for the user to utilize, the system provides a level 1 table with a standard heading, (i.e., a table with multiple columns and one row). The table may then be modified and further customized as desired. Down arrows may be used to add subsequent levels, (i.e., additional rows). The system may only permit one row for level 1 and multiple rows of information for subsequent levels. These rows may correspond to a division, department or other organizational structure pertaining to the company.

Subsequent levels for a company will be for smaller and smaller business units until the names of individual personnel populate the rows. Along with the individual names, the user also creates each individual's title, Basically, the system may permit users to switch from column table headings to row table headings and vice versa Column table headings 510 are shown in FIG. 5B. Row table headings $508_{a-d}$ are shown in FIG. 5E. Upon populating a database, the flexibility between the column table headings 510 and the row table headings $508_{a-d}$ permits users to enter information into the blank table by either the row or the column, whichever is more convenient for the user. If a user querying the system had the proper access, the user may have the system provide all column headings or row headings available for a particular keyword (i.e., company) to allow the user to quickly retrieve or process the information desired.

The centralized database, for example a database accessible via a website, can be maintained by a centralized database management staff or by users with proper passwords. Individual companies may create and maintain their own local database, but permit the database to be searched, via a link to the website. If the centralized database is linked in such a manner to an individual company's database, the system automatically searches the company's database when users query for information from this database. If a company maintains their own database linked to the centralized database, the centralized database management staff does not have the ability to change the actual data.

When a user wants to input information into the centralized database, they must be provided with access to the database. The system may be accessed directly by the user or by following a link to the website. For example, one website may have the URL 20 ReachPeople.com. The name Reach People™ is a trademark of the applicant.

If the user is entering data into the centralized database for the first time, the user is prompted to provide specific information, such as filling in a blank table. In order to ensure the quality and traceability of the information, a method is provided to validate the information. In one embodiment, the user's ISP authenticates the user and confirms the user's e-mail address. In another embodiment, upon entering data, the user is prompted for a method of contact that the user prefers. The user is also prompted for a user name and password. For example, if the user desires to be contacted by e-mail, phone or facsimile, they enter such a preference. Once the user completes the entering of data, the system generates a transaction number and associates that transaction number with each cell of data 10 that the user has entered. The system then sends the transaction number to the user via the particular method of contact chosen by the user. For example, if the user chose to be contacted by e-mail, the system e-mails the transaction number to the user. This completes the input procedure. However, information input into the system is unavailable to other users until the information is validated.

In order to validate the information, the user must log onto the system with their username and password and input the transaction number. All of the information associated with that transaction number will be "released" to all of the users using the centralized database. If the user does not validate the information by providing the transaction number after a predetermined period of time, (which is set by the centralized database management staff, all of the data associated with the particular transaction number is purged from the system.

The disclosed system also provides a method for changing information in the centralized database. The user enters their username and password, and inputs the transaction number. Should the user not provide the correct transaction number and password, the user cannot gain access to making changes. The user will be able to edit all data associated with the transaction number. The system will track and store all data, associated transaction numbers and times, dates and usernames that changed the data. This ensures direct accountability for all data changes. After the user edits the data, the user clicks on "update".

In an alternative embodiment, the system may permit information to be retrieved from, or sent from, anyone without placing any restriction on the user. In this embodiment, a user may become an information supplier and enter unreliable information into the system through the internet.

The system has the ability to run various reports and delete selected information at any time as measures to verify the accuracy of supplied information. The system can automatically review it's data files for inconsistency. The system can automatically use available communication means to contact the information supplier about the inconsistency of the information and request the information supplier confirm the accuracy of the supplied information. For example, if an individual is contacted by an e-mail for the confirmation, the user can respond by e-mail. If the user receives a phone call for confirmation, the system may have an automatic voice system to explain the purpose of the phone call and ask for confirmation on questioned information regarding information in each field in the table. The information supplier can either respond by voice input or manual selection through the telephone button set to acknowledge, correct, incorrect or change. Optionally, before the system makes changes, the system can then block modification to how it received the new information as well as how it receive the original information. When the blocked information is further verified, the system will release such information for modification. The system also has the ability to self-connect the content of its database. For example, the system can update its existing phone numbers to a new phone number in its database if a call to the original phone is placed and the operator advises that there is a new phone number. If there is no forwarding phone number, the system may attempt to re-verify the information by attempting to contact the individual by using one or all of the communication means (i.e., e-mail, fax etc.). If the system makes contact, the system allows the incorrect information to be modified.

In an alternative embodiment, each user can build their own database about themselves and provide a link to the centralized database. The system will search the centralized database for desired information and also any local databases which are linked in such a manner. Those of skill in the art should realize that there are many current methods for linking databases across the internet, and the mariner of linking the databases is not central to the system. A local database may remain only in the user's local computer system. Alternatively, the database may be maintained at the user's internet service provider but may only be accessible when the user is online. A user may set certain restrictions and block selected information, such as credit card information from further modifications. Generally, it can specify certain mandatory basic information that a user has to supply under certain circumstances. The basic information such as the user's name, address, telephone number, "ship to" address (if different then the user's address), credit card number, e-mail address, zip code for mailing purposes, personal profile such as likes, dislikes, age, nicknames, sports, etc.

For example, for online shopping, a user must provide credit card information upon placing an order. In essence, the system can use an established standard format to overlay the data file information into the various fields of a particular website, upon an icon being selected (for example, when a user purchases something). The website may display all information automatically filled in and/or may only prompt the fields that did not match the data file fields, consequently remaining "blank", allowing the user to fill in manually. The term "table" as used herein represents an array of key phrases, since each cell in a table may form the basis of a further search.

In an alternative embodiment, the retrieve and display table may continually appear or be requested by the user to appear when the user is "surfing the web". Once the user invokes the software, the content of the retrieve and display table will be automatically retrieved and updated accordingly. If the user wanted to e-mail, phone or facsimile, the user would simply click the corresponding icon to do so.

It should be noted that a "wildcard" can be used as part of searching phone numbers or facsimile numbers. For example, telephone number 215-756-37** can be used as keyword to search all the phone numbers or facsimile numbers between 215-756-3200 to 215-756-3299. Or if 215-756-3*45 is used for the keyword, then the system will retrieve the phone number's or facsimile number's related to 3045, 3145, 3245, . . . , 3945.

Although the input devices such as keyboard and mouse are used in this specification for explanation purpose, other input methods or devices such as voice input device or touch screen device can also be used with the disclosed system.

The disclosed system can be used as the base for a future internet search engine or directory. A user, by providing phone numbers or facsimile numbers can quickly access all information on the internet and retrieve the information as he specified. Therefore, a user can surf the internet more efficiently.

Figure 6:
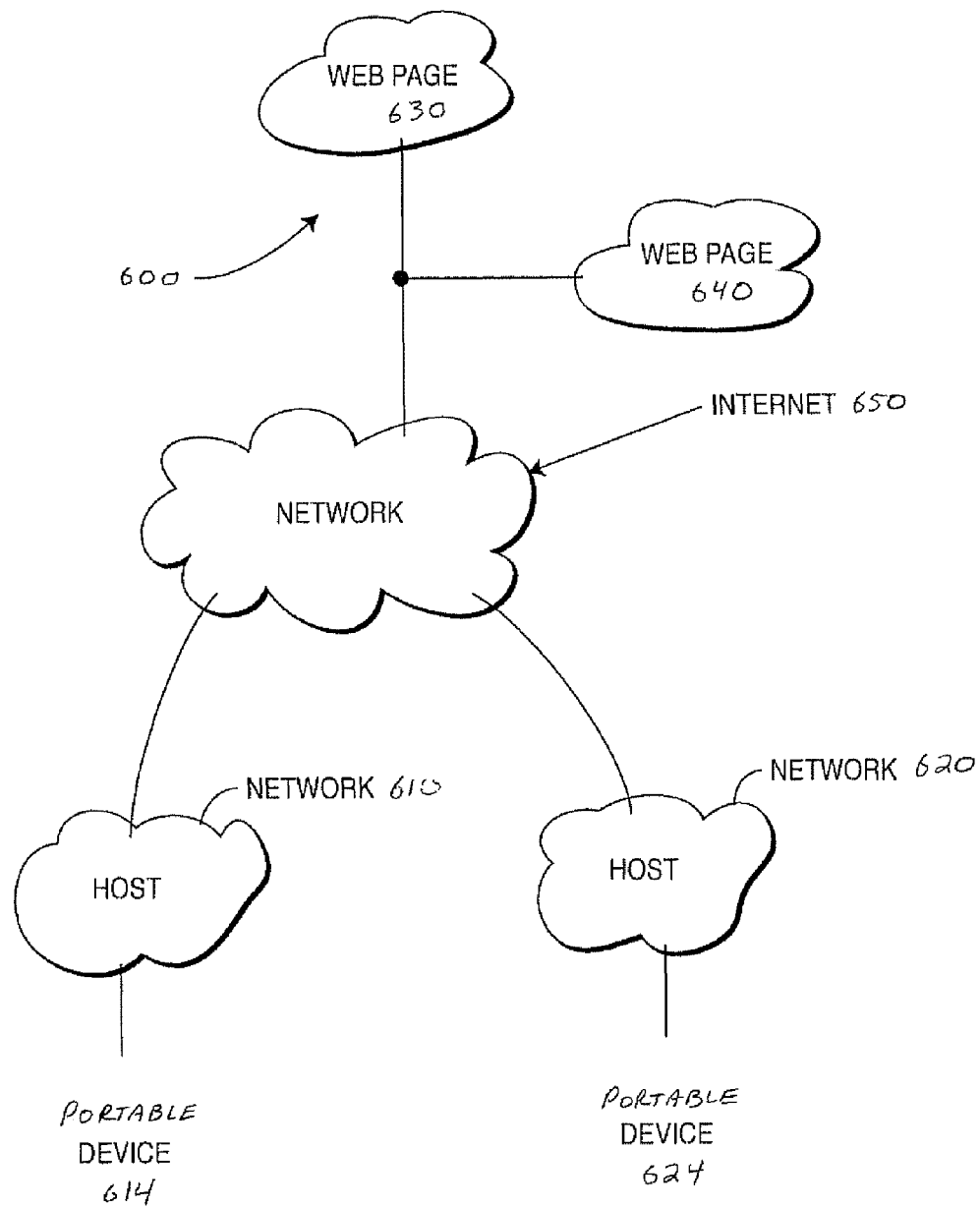
FIG. 6 is a schematic block diagram of a hardware environment consistent with the disclosed systems.

Referring now to FIG. 6, an example system 600 is illustrated. System 600 includes plurality of networks 610, 620 and web pages 630 and 640 are shown connected to the internet 650. A first user (not shown) using device 614 is a resident on a first network 610 and a second user (not shown) using device 624 is a resident on a second network 620.

Example system 600 includes additional hardware, namely portable device 614, which is consistent with all embodiments discussed herein. Portable device 614 may be a portable storage device or a portable communication device such as a mobile telephone, a Portable Digital Assistant ("PDA"), a transponder, a memory stick or an implanted chip, for example. A portable device 614 provides storage capability which may store information or links to information which comprise at least a portion of the information to be maintained and/or searched. As previously described with respect to other embodiments, the information to be maintained and/or searched may reside in a single database or may be distributed among a plurality of databases. Also as previously described with respect to other embodiments, multiple users and institutions may be linked together. Some users may choose to use the portable device to help facilitate those links when they are not accessible to the Internet (i.e., online). In other words, the portable device extends the reach of the ReachPeople system to anywhere and everywhere that the portable device may be taken. It further converges all communications mediums together where one can send/store/access/retrieve various information or links to information at a later point in time over the Internet.

Consider an example embodiment in which the first and second users are both carrying portable storage devices 614 and 624. The first user possesses PDA 614 on which he maintains all of his preferred directory information, and the second user possesses mobile telephone 624 on which she maintains all of her preferred directory information.

Information stored on portable devices 614 and 624 may include information which is redundantly stored on another computer or network controlled or accessed by the first and second users, respectively. For example, the mobile telephone may have access to information stored with a third party, such as a mobile telephone service provider or an Internet web site operator.

Each user, upon deciding to include the other's contact information in his/her preferred directory information, may initiate an exchange of contact information from his/her portable storage device 614 and 624. According to the example embodiment, each user may exchange contact information or a link to the contact information. The exchange of contact information or a link to contact information may be effected either automatically or manually.

According to one embodiment using the portable device, a user who wishes to provide information to another can predefine the information which is to be transferred. More specifically, a user may wish to provide all information in his/her database or just a subset of the information. In the ReachPeople system, for example, the user can create a database containing a wide variety of personal information. The user may then, for example, define a subset of the personal information pertaining to medical information, or the user may define a business card containing business contact information which is a subset of the personal information. Upon defining a particular subset of information, the user can choose to only exchange/share the defined subset of information with another user. In one embodiment, a user may identify which of a plurality of predefined subsets to share/exchange by pressing an associated button or using a GUI on the portable storage device.

The embodiment using the portable storage device can effect an automatic transfer, whereby the exchange is pre-authorized enabling the receiving party to receive the information or link without validation from the sending party. Upon such an automatic transfer, both parties would have access to each others information in the ReachPeople system. In a manual transfer using the portable storage device, the exchange may not be completed until the sending user and/or receiving user authorizes the transfer. In one embodiment, one user may be pre-set for automatic transfer mode while the second user may be pre-set for manual transfer mode. Additionally, a user can set automatic mode for receiving and manual mode for sending or vice versa. In an embodiment, the initiating party's request from the portable storage device for a link may be displayed in the receiving party's ReachPeople's system in the "Links Pending" section waiting for the receiving party to validate the link, thereby allowing the parties to access each others information.

Figure 7:
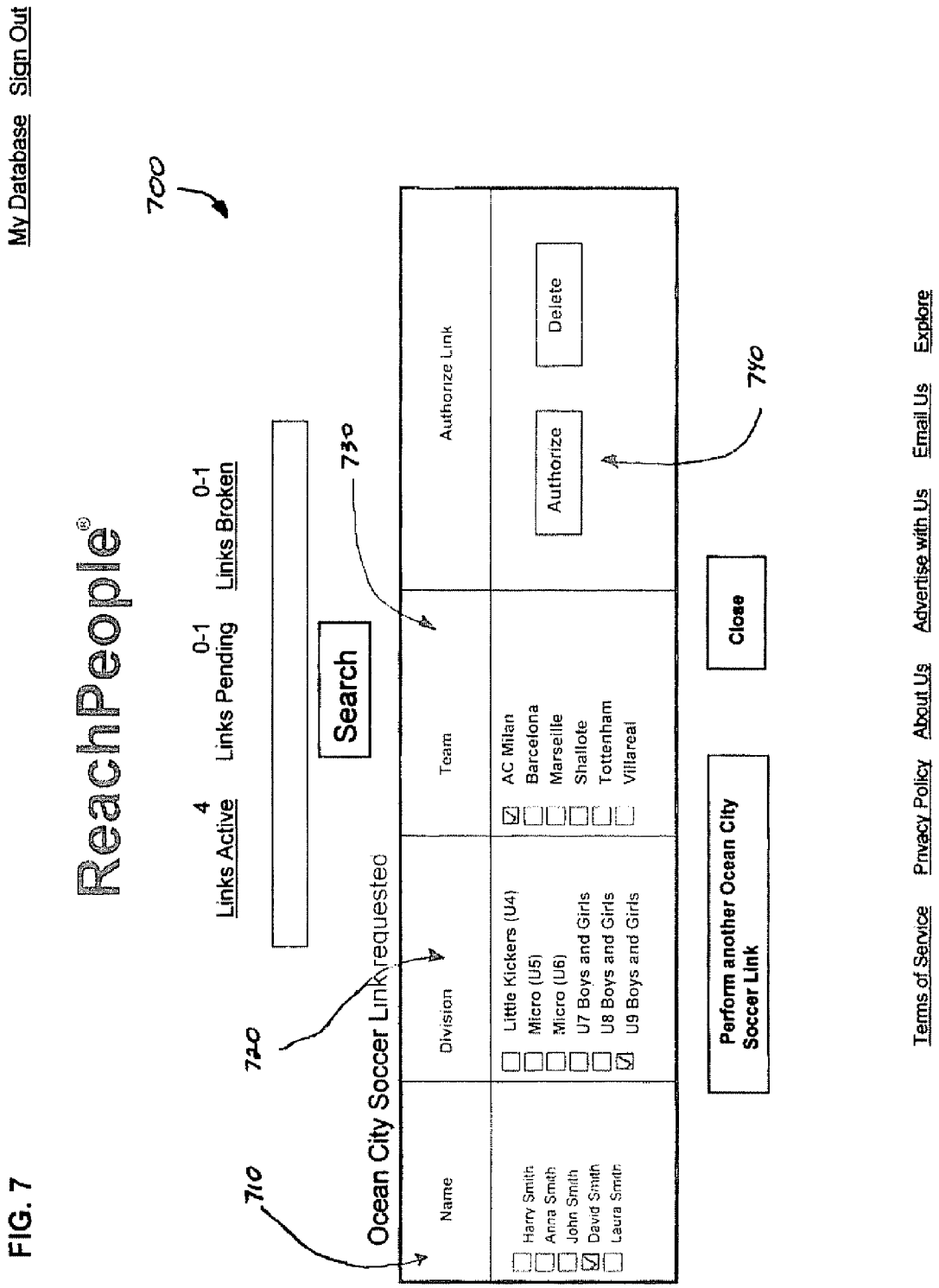
FIG. 7 is a computer screen display illustrating a Links Pending window.

FIG. 7 illustrates an example "Links Pending" window 700. Links Pending window 700 indicates which links are pending for a user who is linking to a soccer group institutions. The user selects a name 710 from his database. In the example, the selected user is a family member. The user then selects chooses a "Division" 720 and a "Team" 730. In an alternative embodiment, the institution may not allow the user to choose Division and Team. Instead, the institution would assign the user to a particular Division and Team, when the institution authorizes the link from their end. In the illustrated embodiment, the institution requires that the individual first authorize/validate the link using button 740 so that the institution would be the last side to finalize/authorize/validate the link allowing the institution to make any changes to the information associated with the link. For example, the institution may change the Division and/or Team following the user's authorization.

Optionally, the system may require either or both the initiator (sending user), and receiving/target user to authorize/validate the link in the ReachPeople system. Further, if one user is not connected to his/her network at the time of a transfer or link request, the system or device may hold the link until the offline user logs on or uploads the information from the portable storage device to his/hey network, and then the link may be listed as a pending link in the ReachPeople System. For example, if a link to contact information was transferred to a user's PDA, when the user connects/uploads data from his/her PDA via the Internet, the system may generate a link pending request in the ReachPeople system for either or both the initiator of the transfer and the receiving party. Various types of chimes and/or verbal indicators may be useful features. For example, a voice indicator may describe an activity once it has been performed, such as "Business information has been transferred to John Smith." or "Information received from John Smith."

In one embodiment, a user can swap information with another user by passing their portable storage devices within a predefined distance such as several inches or many feet. The portable storage device may have a touch screen that asks what information he/she wants to transfer, such as if the link is a business link, medical link, or full link. The user may indicate the type of link being provided by selecting a button or pressing the screen, for example. Either user may have to enter some basic information about the party that they want to request a link with such as their name; and the portable storage device can then provide the available choices from which the user may then choose.

For example, if a user was at a business convention and met John Smith, the user may begin typing in John's first name. All matches that started with "J" in the user's vicinity, based on a location or a predetermined distance, would appear on the display of the user's portable device. The user could then request to exchange information or links by selecting the appropriate entry from the list of displayed matches. Alternatively, as the user continues typing "JO", the subset of all names that started with "JO" would appear thereby further refining the list of matches from which the user may select. In addition, the portable storage device can provide an audible, vibration or visual confirmation of a link and ultimate exchange of information. Said audible, vibration, or visual confirmation may be different depending if you were the sender or receiver. For example, a user may pre-set their device to make one sound for receiving and make another sound when sending. In another example, the device may specifically state via voice response or visual response what function was or will be performed. For example, the device may say via voice of on a visual screen "Sent contact information to John Smith"; "Please press number 1, to send information to John Smith"; "Received information from John Smith"; or "Received request from John Smith for a link, please press 1 to accept". Optionally, these requests can be held at a pending status and can be accessed from the device or uploaded to a computer or network at a later time.

It should be noted that regardless of whether the data transferred from the portable storage device is information, such as contact information, or a link to information, the ReachPeople system may enable a user to limit the use of such data by the receiving or target user. For example, a sending user may limit use of the information to personal use by the receiving user, prohibiting the receiving user passing on the same link or information to other users It should also be noted that a user may use a portable device such as 614 or 624 to transfer information including links and information from links which is redundantly stored by the portable device, or stored off site from the portable device.

Information and links to access information may be up/downloaded onto the portable storage device in a number of ways. For example, transponders, PDAs and other portable devices may employ a USB port to transfer information. Alternatively, devices may employ FireWire, Blue Tooth or any other known wired or wireless transmission mechanisms.

Of course, embodiments of the system using the transponder are not limited to maintaining and searching directory information. As set forth above, the described systems and methods may be used to maintain, link and facilitate searching of non-directory information such as medical, financial or other information.

In an embodiment in which the present information maintains, links and facilitates searching of medical information, the system may employ a portable device, such as a transponder, for example, for maintaining a database of personal medical information. The transponder may store information or links to information relating to patient information, medical diagnoses, test results, medications, allergies, medical insurance providers, medical professionals, covered medical procedures and expenses, and other information relating to a user's health care.

It is envisioned that such information, due to its sensitive and private nature, may be subject to a variety of security precautions. For example, the data and links stored by the portable device may be encrypted, subject to password protection, subject to biometric verification by or from the user, subject to security and/or subject to read-only access. In one embodiment, the user may provide biometric verification when Lip/downloading to/from the device. The biometric verification may be part of the password stored on one or more of the computer, the network or the device. The biometric verification is matched before providing up/download access to the device. Optionally, the device may attempt to recognize the computer and/or the network. The device may require validation from a particular website prior to allowing uploading and downloading access to the device. The system may create parameters such that at the time the device is connecting to a computer/network, the information stored on the device may be erased, destroyed, corrupted or reformatted, such as by filling the memory with "010101 . . . ." Further, the system may be configured such that a user can direct the system to automatically erase, destroy, corrupt or reformat data stored on a portable device in the event the device detects an attempt by another to tamper with or otherwise access the data without proper authorization.

For example, the ReachPeople system may only allow the information to be exported to the portable storage device in a read only format Optionally, the ReachPeople system may allow the upload/download of information to/from a portable storage device with additional parameters such as noting what computer or IP address was used when uploading/downloading the information. The ReachPeople system may also require a password prior to uploading/downloading the information to/from the portable storage device. The ReachPeople system may install a file on either or both the computer used to upload/download the information and the portable storage device. Said file could include the password information such as a key that must match a key on the ReachPeople system or two keys taken together from both the computer and portable storage device that must match a key in the ReachPeople system before allowing the information to be uploaded off of the portable storage device. Should someone try to upload the information from the portable storage device (along with any new information that had been transferred to it) to a different computer the portable storage device can be programmed to not upload the information. Further, the portable storage device can automatically delete and/or overwrite the information with or without a warning message.

In one embodiment, the system may employ layered or multi-factor authentication. The system may further include a log to track and identify, among other things, every link or link request involving a particular device and the associated information transferred. In the event of a portable device failure or breach, the log may be stored in a location other than on the portable device, such as in another device, computer or network, to improve security. For example, the log may be maintained at ReachPeople website requiring its authorization prior to accessing the device and uploading or downloading.

In another embodiment, information or links to information may be transferred in conjunction with a telephone call, including a call handled by a voicemail system or answering machine. For example, two users conducting a telephone conference using a Voice Over IP ("VOIP") connection may exchange information during the call employing otherwise unused bandwidth to effect the transfer. As described above, the transfer may be initiated, for example, upon the issuance of a voice command; based on the proximity of a transponder to the telecommunication device; or by a user pressing a button on the telecommunication device or computer. It should be noted that such a transfer of information may be possible even if only one party is employing a VOIP connection. Further, such transfers are also envisioned through the use of a digital answering machine, e-mail system, radio/television broadcast or other communications device.

The disclosed system has useful application in a number of data transfer environments. For example, the disclosed system is may be used in cooperation with broadcast media receivers. A user may press a button on a portable device to receive or transmit a link or link request associated with a broadcast advertisement or other event. If a user was watching a commercial or listening to the radio and a product was advertised that interested the user, said user can press a button to capture the information (e.g. authorizing receipt of the information) or a link to the information that they can access later when connected to the Internet. In another example application, the system can be used to receive redeemable coupons. In such an application, a user may press a button on a portable device to receive coupon information. The redeemable coupons may be allowed to be directly submitted from the device to a particular store. The store may be able to capture or receive various information from the device identifying the user and where the coupon was originated such as from a particular a radio or television commercial.

Alternatively, the redeemable coupon may have to be downloaded through a link over the Internet. The website providing the redeemable coupon may capture information from the user including the user's contact information and which commercial the user had watched or listened to. In this example, the user may be prompted to establish a link with the advertiser for purposes of sharing information from the advertiser, to the advertiser or both the user and advertiser sharing information with the other party. In yet another example application, the system may enable a user to register a vote for a particular event, such as a television program, feedback for advertised products/commercials. Again, the user may be prompted to establish a link with the television program or company over the Internet. Establishing a link includes using the ReachPeople system to facilitate the linking process. In such applications, the portable device may employ RF, IR or any other wireless communication technology. Additionally, the portable device may utilize wired communication technology to capture the information (e.g., it may have a wire connecting to the broadcast media receiver).

In one embodiment, a user or system administrator, based upon predefined settings or parameters, may allow parties that have established links with one another to utilize the resources of each other's device, computer or network. For example, to expedite an emergency notification, another's CPU time or Internet capability may be utilized. In this embodiment, each device provides redundancy of resources to the others. Of course, the system may further track the distributed processing to validate that duplicative messages are not sent or received.

In another example embodiment of the system, users watching television or listening to the radio may register themselves using their contact information or their payment information such as credit card information with an institution. There are numerous benefits to the broadcasting or advertising institution, but the user also benefits from the centralized maintenance of all such registrations. Further, should the user need to modify his/her-information, the user would do it once and all institutions with which lie/she had registered, assuming that they had access to that information, would have the updated information. The user may, at anytime, access the list and drill down using the links to further access information from a particular entity. For example, if the user desired to communicate with the entity, the user can drill down into the entity and then choose a particular unique identifier and communicate with the entity (e.g., customer service). In another example, if the user was interested in a particular ad regarding a boat, the user can capture the link with their portable device and access the link at any point later thru an Internet connection to learn more information about the boat. The boat manufacturer or dealer may capture what ad the user listened to. It further may ask for your contact information and incentivize the user by offering a special discount upon the user doing so.

In another example embodiment, a user viewing a television show such as American Idol may download information, such as the voting information representing the respective idols or a link to said information, for example. If it were a link to the information, the user would then find the information on the Internet using the link. This may be immediate if the user's portable device is Internet enabled or may be done at later time when the portable device becomes enabled or connecting the device to another device that is enabled to the Internet (e.g., connecting the device to upload the information or link to a computer that has access to the Internet). Upon going there or doing so, the user can modify the information (e.g., choose the number of votes per idol) and then send the information back to the website. The website may charge a fee per vote. The payment for the charge may be provided by your payment information in your link being provided to the website. The website may, each week, update the information allowing the user to click the same link and have the new/revised information (C g, to vote on the current week of idols).

In another example embodiment, the user may view or hear a commercial advertising a television show or movie. Or, the user may start to watch a television show but wants to stop watching the show for viewing a later date. Or the user wants to send a link for access to (a copy of) the commercial or television show or movie over the Internet to a friend The user can capture a link to the commercial, television show or movie and access a download to the television show or movie over the Internet. Or, the user may send the captured link to a friend allowing them the ability to access the information at the link.

In each of the above examples, the user downloads the information (or a link to the information), can modify or respond to the information and sends it back over an Internet connection to an associated website of the institution. As one skilled in the art understands, this invention is applicable for a user to capture information or links to information from advertisements for joining social groups, political parties, class action suits, blogging groups just to mention a few.

In yet another example, a manufacturer in a commercial advertisement can provide information to a viewer, such as via the portable device of the user. The information may be a link to the manufacturer's website. The website provides a list of participating dealers to the user. Upon the user identifying the user's area, the corresponding dealers in that area are provided. The user may identify the area, for example, by authorizing a link with their contact information or by providing an address or zipcode.

In the ReachPeople system, a user may provide contact information that includes multiple fields, such as home telephone number, home e-mail address, business telephone, business e-mail address, fax number, mobile telephone number, etc. An emergency communication may be configured to be delivered to devices identified by one, multiple or all of a receiving user's defined contact fields.

Utilizing a device to exchange information provides a number of benefits when the system is employed to maintain personal medical information. For example, medical providers will have access to greater amounts of historical information providing a patient's medical history that is not only more complete but also easier to obtain. Another benefit of utilizing the present invention in the context of maintaining personal medical information is that medical diagnoses will be generally more reliable due to the availability of more complete medical histories. Yet another benefit is that medical insurers will be able to more efficiently and reliably approve/reject claims. For example, a user has a scheduled doctor's appointment. As described above, the device may request information or link with the doctor. Or, it can accept information or a request for link from the doctor. Optionally, the device may allow you to access a link to your information while in the doctor's office. In another example, prior to the appointment to see his/her doctor, the user downloads his/her information to their device that includes their insurance information and/or a link to their insurance company. It further may include their extended medical history as well as their family's extended medical history (note the user had previously linked their medical information with family members using the ReachPeople system) or a link to the medical history. Depending on the parameters, the doctor may only be able to review the medical history in a read only format. Optionally, the doctor can upload some or all of the information or a link to the information from the device. The doctor can review various medical reports from other doctors that may have been linked to the user and said information or link to information included on the device. Optionally, the device can provide a link to the doctor so that all of the information is available/accessible to said doctor over the Internet. The device may allow a link to be formed between multiple parties. In this present embodiment, the device may facilitate a link between the doctor, insurance company and pharmacy allowing the insurance company, doctor and pharmacy to share private information among themselves that is unavailable to the user. By allowing numerous parties to be linked and share selected information, it will streamline the efficiency of the healthcare system. This invention can resolve the current fragmented state of the healthcare system which is still, for the most, part paper-based, and often inaccessible from one health care provider to another. It will also increase safety among hospitals, clinics, doctors, nurses, pharmacies.

Although a number of interface means have been described herein, the present invention is not limited to any specific interface means. For example, the present invention may employ keyboards, keypads, LCD displays, head-up displays, audio interfaces, voice-recognition interfaces and any known device capable of acting as a user interface.

Although the invention has been described in part by making detailed reference to the preferred embodiment, such detail is intended to be instructive rather than restrictive. It will be appreciated by those skilled in the art that many variations may be made in the structure and mode of operation without departing from the spirit and scope of the invention as disclosed in the teachings herein.

What is claimed is:

1. A method for exchanging personal information between portable devices, comprising:
   detecting, with a first portable device, a plurality of portable devices in a vicinity of the first portable device;
   presenting with the first portable device a list comprising identifiers for the plurality of portable devices that are detected in real-time in the vicinity of the first portable device;
   receiving user input via the first portable device that selects an identifier for a second portable device associated with a second user from the presented list;
   transmitting personal information, about a first user associated with the first portable device, from the first portable device to the second portable device associated with the second user in response to said receiving user input and passing the second portable device within several inches of the first portable device; and
   receiving, with the first portable device from the second portable device, a Uniform Resource Locator (URL) link to personal information about the second user of the second portable device;
   wherein the detecting comprises detecting the plurality of portable devices based on whether ones of the plurality of portable devices are within a predefined distance of the first portable device.

2. The method of claim 1 wherein the personal information comprises medical information for the first user.

3. The method of claim 1 wherein the personal information comprises contact information for the first user.

4. The method of claim 1 further comprising:
   presenting on the first portable device a request for authorization to transmit the personal information to the second portable device,
   wherein said transmitting personal information occurs in response to receiving affirmation to the request for authorization via a user input of the first portable device.

5. The method of claim 1, further comprising: connecting to a global communication network with the first portable device; and
   retrieving the personal information about the second user from the global communication network via the received URL link.

6. The method of claim 1 wherein the transmitting the personal information about the first user comprises transmitting, from the first portable device to the second portable device, a Uniform Resource Locator (URL) link to the personal information.

7. The method of claim 6, wherein the URL link provides a reference for accessing updated personal information about the first user.

8. The method of claim 4, wherein the receiving affirmation includes receiving biometric data from the first user with the first portable device.

9. An apparatus for exchanging personal information, comprising:
   a processor;
   an input device;
   an output device;
   a receiver;
   a transmitter; and
   a memory operatively connected to the processor, the memory storing instructions operable with the processor to cause the processor to:
     detect, via the receiver, a plurality of portable devices in a vicinity of the receiver;
     present on the output device, a list comprising identifiers for the plurality of portable devices that are detected in real-time in the vicinity of the receiver;
     receive, from the input device, a selection for an identifier from the list that identifies a portable device from the plurality of portable devices; and
     transmit via the transmitter, personal information about a user of the apparatus to the identified portable device in response to the identified portable device being passed within several inches of the apparatus;
   wherein the instructions further cause the processor to detect, via the receiver, the plurality of portable devices based on whether ones of the plurality of portable devices are within a predefined distance of the receiver; and wherein the instructions further cause the processor to transmit to the identified portable device, via the transmitter, a Uniform Resource Locator (URL) link to the personal information for the user of the apparatus.

10. The apparatus of claim 9, wherein the instructions further cause the processor to receive from the identified portable device, via the receiver, a Uniform Resource Locator (URL) link to personal information about a user of the identified portable device.

11. The apparatus of claim 9, wherein the personal information comprises medical information for the user of the apparatus.

12. The apparatus of claim 9, wherein the personal information comprises contact information for the user of the apparatus.

13. The apparatus of claim 9, wherein the instructions further cause the processor to present, on the output device, a request for authorization to transmit the personal information to the identified portable device, and transmit, via the transmitter, the personal information in response to affirmation to the request for authorization received via the input device.

14. The apparatus of claim 9, wherein the transmitter is further configured to transmit the personal information to the identified portable device via a global communication network.

15. The apparatus of claim 9, wherein the URL link provides a reference for accessing updated personal information about the user of the apparatus.

16. The method of claim 1 wherein:
the first portable device comprises a first telephone; and
the second portable device comprises a second mobile telephone.

17. A method for exchanging personal information between portable devices, comprising:
detecting, with a first portable device, a plurality of portable devices in a vicinity of the first portable device;
presenting with the first portable device a list comprising identifiers for the plurality of portable devices that are detected in real-time in the vicinity of the first portable device;
receiving user input via the first portable device that selects an identifier for a second portable device associated with a second user from the presented list;
transmitting personal information, about a first user associated with the first portable device from the first portable device to the second portable device associated with the second user in response to said receiving user input and passing the second portable device within several inches of the first portable device;
receiving, with the first portable device from the second portable device, a Uniform Resource Locator (URL) link to personal information about the second user of the second portable device;
wherein the plurality of portable devices each comprises a mobile telephone.

18. A method for exchanging personal information between portable devices, comprising:
detecting, with a first portable device, a plurality of portable devices in a vicinity of the first portable device;
presenting with the first portable device a list comprising identifiers for the plurality of portable devices that are detected in real-time in the vicinity of the first portable device;
receiving user input via the first portable device that selects an identifier for a second portable device associated with a second user from the presented list;
transmitting personal information, about a first user associated with the first portable device from the first portable device to the second portable device associated with the second user in response to said receiving user input and passing the second portable device within several inches of the first portable device;
receiving user input via the first portable device that specifies search criteria for portable devices;
generating the list such that the list comprises identifiers for portable devices that both satisfy the received search criteria and are in the vicinity of the first portable device; and
receiving, with the first portable device from the second portable device a Uniform Resource Locator URL link to personal information about the second user of the second portable device.

19. The method of claim 17, further comprising: connecting to a global communication network with the first portable device; and
retrieving the personal information about the second user from the global communication network via the received URL link.

20. The method of claim 17, further comprising:
presenting on the first portable device a request for authorization to transmit the personal information to the second portable device,
wherein said transmitting personal information occurs in response to receiving affirmation to the request for authorization via a user input of the first portable device.

21. The method of claim 17, wherein the transmitting the personal information about the first user comprises transmitting, from the first portable device to the second portable device, a Uniform Resource Locator (URL) link to the personal information.

22. The method of claim 18, further comprising: connecting to a global communication network with the first portable device; and retrieving the personal information about the second user from the global communication network via the received URL link.

23. The method of claim 18, further comprising:
presenting on the first portable device a request for authorization to transmit the personal information to the second portable device,
wherein said transmitting personal information occurs in response to receiving affirmation to the request for authorization via a user input of the first portable device.

24. The method of claim 18, wherein the transmitting the personal information about the first user comprises transmitting, from the first portable device to the second portable device, a Uniform Resource Locator (URL) link to the personal information.

* * * * *